(12) United States Patent
Lee et al.

(10) Patent No.: US 9,120,836 B2
(45) Date of Patent: *Sep. 1, 2015

(54) METHOD FOR PREPARING TRANSITION METAL COMPLEXES, TRANSITION METAL COMPLEXES PREPARED USING THE METHOD, CATALYST COMPOSITION CONTAINING THE COMPLEXES

(75) Inventors: Choong-Hoon Lee, Daejeon (KR); Eun-Jung Lee, Daejeon (KR); Seung-Whan Jung, Suwon-si (KR); Jung-A Lee, Daejeon (KR); Bo-Ram Lee, Seoul (KR); Bun-Yeoul Lee, Suwon-si (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,740

(22) Filed: Mar. 22, 2011

(65) Prior Publication Data

US 2011/0177935 A1 Jul. 21, 2011

Related U.S. Application Data

(62) Division of application No. 12/448,825, filed as application No. PCT/KR2007/006940 on Dec. 28, 2007, now Pat. No. 7,932,207.

(30) Foreign Application Priority Data

Jan. 10, 2007 (KR) .................. 10-2007-0003071

(51) Int. Cl.
*B01J 31/14* (2006.01)
*C07F 7/28* (2006.01)
*B01J 31/18* (2006.01)
*C07F 7/00* (2006.01)
*C07C 211/48* (2006.01)
*C07F 17/00* (2006.01)

(52) U.S. Cl.
CPC ...................................... *C07F 17/00* (2013.01)

(58) Field of Classification Search
CPC .................................. C07F 17/00; B01J 31/14
See application file for complete search history.

(56) References Cited

U.S. PATENT DOCUMENTS

| 6,090,962 | A | 7/2000 | Rosen | |
|---|---|---|---|---|
| 6,548,686 | B2 | 4/2003 | Nabika et al. | |
| 7,105,690 | B2 | 9/2006 | Schottek et al. | |
| 7,439,378 | B2 | 10/2008 | Park et al. | |
| 7,915,360 | B2 * | 3/2011 | Hong et al. | 526/161 |
| 7,928,256 | B2 * | 4/2011 | Lee et al. | 556/53 |
| 8,048,973 | B2 * | 11/2011 | Lee et al. | 526/161 |
| 2003/0065203 | A1 | 4/2003 | Wilson et al. | |
| 2007/0225158 | A1 * | 9/2007 | Lee et al. | 502/152 |

FOREIGN PATENT DOCUMENTS

| CN | 1049849 | 3/1991 |
|---|---|---|
| CN | 1444592 A | 9/2003 |
| JP | 3-163088 A | 7/1991 |
| JP | 8-325283 A | 12/1996 |
| KR | 10-2002-0000120 | 1/2002 |
| KR | 10-0515596 | 9/2005 |
| KR | 10-2007-0072236 | 6/2007 |
| WO | WO 2006/022355 A1 | 3/2006 |

OTHER PUBLICATIONS sciFinder search history.*
Esteruelas et al. Organometallics, 2005, 24, 5084-5094.*
Wu et al. Organometallics, 26(27), 6686, 2007.*
Enders et al., Chirale Titan-und Zirkoniumkomplexe mit dem 1-(8-Chinolyl)-2,3-dimethylcyclopentadienyl-Liganden[1], Journal of Organometallic Chemistry 549 (1997) pp. 251-256, Heidelberg, Germany.
M. Enders et al., Synthesis of Main Group and Transition Metal Complexes with the (8-Quinolyl)cyclopentadienyl Ligand and Their Application in the Polymerization of Ethylene, Organometallics 23 (2004) pp. 3832-3839, Heidelberg, Germany.
Dae Joon Cho et al., o-Phenylene-Bridged Cp/Amido Titanium Complexes for Ethylene/1-Hexene Copolymerizations, Organometallics 25 (2006) 2133-2134, Chung-nam, Korea.
Joung et al., Organometallics 25 (2006) pp. 5122-5130.
O-Phenylene-bridged Cp/sulfonamido titanium complexes for ethylene/1-octene copolymerization; Joe, Dae June; Wu, Chun Ji; Bok, Taekki; Lee, Eun Jung; Lee, Choong Hoon; Han, Won-Sik; Kang, Sang Ook; Lee, BunYeoul; Dalton Transactions (2006), (33), 4056-4062.
A Novel Phenolate "Constrained Geometry Catalyst System. Efficient Synthesis, Structural Characterization, and a-Olefin Polymerization Catalysis"; T. J. Marks et al.; Organometallics 1997, 16, 5958-5963.
Dae Joon Cho, et al., "o-Phenylene-Bridged CP/Amido Titanium Complexes for Ethylene/ 1-Hexene Copolymerizations", Organometallics, Feb. 25, 2006, pp. 2133-2134.
Cho et al., Organometallics, Mar. 31, 2006, vol. 25, p. 2133-2134.
Katritzky et al., Terahedron Letters, 1985, vol. 26, p. 5935-5938.
Nishida et al., Bull. Chem. Soc. Jpn., 1988, vol. 61, p. 3919-3923.
Murata et al., J. Am. Chem. Soc., 1985, vol. 107, p. 6317-6329.
Sugawara et al., J. Am. Chem. Soc., 1985, vol. 107, p. 1329-1339.
Rapoport et al., "Fluoradene", (JACS, 82,934,1959).

* cited by examiner

*Primary Examiner* — Yun Qian
(74) *Attorney, Agent, or Firm* — Dentons US LLP

(57) ABSTRACT

The present invention provides a novel transition metal complex where a monocy-clopentadienyl ligand to which an amido group is introduced is coordinated, a method for synthesizing the complex, and olefin polymerization using the same. The method for preparing a transition metal complex according to the present invention comprises a step of blocking a by-reaction of a nitrogen atom using a compound containing a protecting group, and thus it is possible to prepare a transition metal complex in a simpler manner in a high yield. Further, the transition metal complex according to the present invention has a pentagon ring structure having an amido group connected by a phenylene bridge in which a stable bond is formed in the vicinity of a metal site, and thus, sterically monomers can easily approach the transition metal complex.

6 Claims, No Drawings

METHOD FOR PREPARING TRANSITION METAL COMPLEXES, TRANSITION METAL COMPLEXES PREPARED USING THE METHOD, CATALYST COMPOSITION CONTAINING THE COMPLEXES

This application is a divisional of U.S. patent application Ser. No. 12/448,825, filed on Jul. 9, 2009 now U.S. Pat. No. 7,932,207, which claims priority to International Application No. PCT/KR2007/006940, filed on Dec. 28, 2007 and claims priority benefits from Korean Patent Application No. 10-2007-003071, filed on Jan. 10, 2007, the entire contents of which are fully incorporated herein by reference.

TECHNICAL FIELD

The present invention relates to a method for preparing a transition metal complex, transition metal complex prepared using the method, and a catalyst composition containing the transition metal complex.

BACKGROUND ART

In the early 1990s, Dow Chemical Co. disclosed [Me$_2$Si(Me$_4$C$_5$)NtBu]TiCl$_2$ (Constrained-Geometry Catalyst, hereinafter simply referred to as CGC) (U.S. Pat. No. 5,064,802). CGC shows excellent properties in a copolymerization reaction of ethylene and α-olefin, as compared to conventional metallocene catalysts. Its main two excellent properties can be summarized as follows: (1) CGC can be used to form high molecular weight polymers due to its high activity at high polymerization temperature, and (2) CGC can be used for copolymerization of α-olefin having large steric hindrance, such as 1-hexene and 1-octene. As many useful properties of CGC are disclosed, in addition to these properties described above, research into synthesis of CGC derivatives as a polymerization catalyst is increasingly conducted in academic and industrial fields.

As one example of such approaches, synthesis of metal compounds comprising other various bridges instead of a silicon bridge and containing a nitrogen substituent, and polymerization using these metal compounds were performed. Examples of such metal compounds include Compounds (1) through (4) (Chem. Rev. 2003, 103, 283).

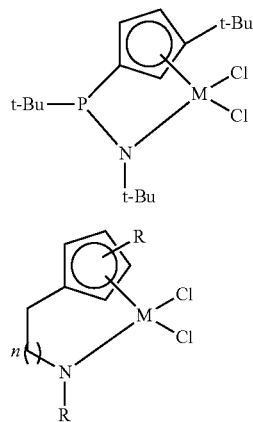
(1)
(2)

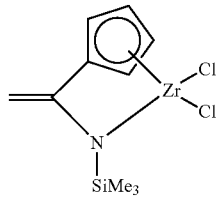
(3)

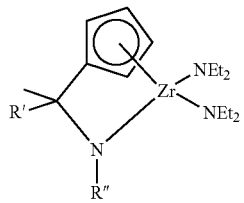
(4)

Compounds (1) through (4) respectively contain a phosphorus bridge (1), an ethylene or propylene bridge (2), a methyllidene bridge (3), and a methylene bridge (4), instead of the silicon bridge of the CGC structures. However, these compounds could not show enhanced activity, copolymerization performance, or the like when ethylene is polymerized or when ethylene and α-olefin are copolymerized, as compared to CGC.

In another example of the approaches, a great number of compounds, in which an amino ligand in CGC is replaced with an oxido ligand, have been synthesized. There have been attempts to use such compounds for polymerization. Examples of such compounds include those represented by Formulae below:

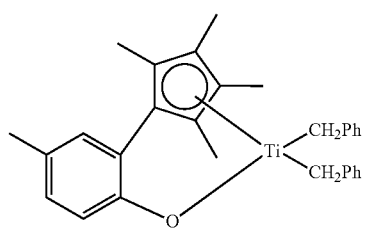
(5)

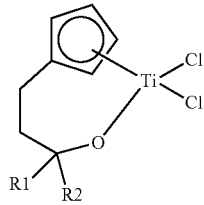
(6)

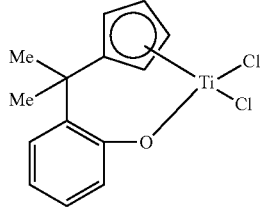
(7)

-continued (8)

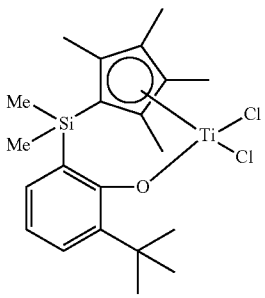

In Compound (5), which was developed by T. J. Marks, et al., a cyclopentadiene (Cp) derivative is bridged to an oxido ligand by an ortho-phenylene group (*Organometallics* 1997, 16, 5958). A compound having the same bridge and polymerization using the complex were reported by Mu et al. (*Organometallics* 2004, 23, 540). A compound in which an indenyl ligand is bridged to an oxido ligand by an ortho-phenylene group was reported by Rothwell, et al. (*Chem. Commun.* 2003, 1034). In Compound (6), which was reported by Whitby, et al., a cyclopentadienyl ligand is bridged to an oxido ligand by three carbon atoms (*Organometallics* 1999, 18, 348). As reported, Compound (6) shows activity in syndiotactic polystylene polymerization. Similar compounds were also reported by Hessen, et al. (*Organometallics* 1998, 17, 1652). Compound (7), which was reported by Rau, et al., showed activity when it is used for ethylene polymerization and ethylene/1-hexene copolymerization at a high temperature and a high pressure (210° C., 150 Mpa) (*J. Organomet. Chem.* 2000, 608, 71). Synthesis of Compound (8), which has a similar structure to the compound, and a high-temperature and high-pressure polymerization using the compound was filed in patent application by Sumitomo Co. (U.S. Pat. No. 6,548,686).

However, only sane of these catalysts as described above are used in commercial plants. Accordingly, there is a need to develop a catalyst exhibiting enhanced polymerization performance, and a method for simply preparing the catalyst.

DISCLOSURE OF INVENTION

Technical Problem

It is a first object of the present invention to provide a method for preparing a novel transition metal complex.
It is a second object of the present invention to provide a transition metal complex prepared using the method.
It is a third object of the present invention to provide a catalyst composition comprising the transition metal complex.

Technical Solution

According to a first aspect of the present invention, there is provided a method for preparing a novel transition metal complex, comprising the steps of:
(a) reacting an amine-based compound represented by Formula 1 below with an alkyl lithium and then adding a compound containing a protecting group (—$R_0$) thereto to prepare a compound represented by Formula 2 below;
(b) reacting the compound represented by Formula 2 with an alkyl lithium, and adding a ketone-based compound represented by Formula 3 below to prepare an amine-based compound represented by Formula 4 below;
(c) reacting the compound represented by Formula 4 with n-butyl lithium to prepare a dilithium compound represented by Formula 5 below; and
(d) reacting the compound represented by Formula 5 with $MCl_4$ (M=Ti, Zr, or Hf) and an organic lithium compound to prepare a transition metal complex represented by Formula 6 below:

<Formula 1>

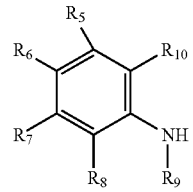

<Formula 2>

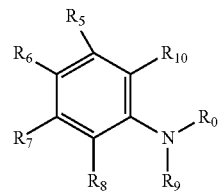

<Formula 3>

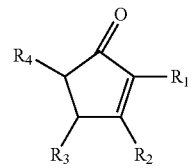

<Formula 4>

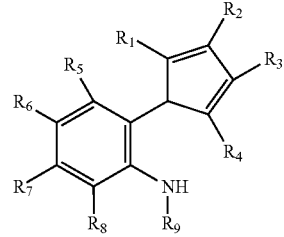

<Formula 5>

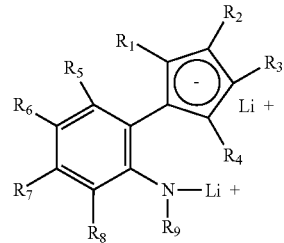

<Formula 6>

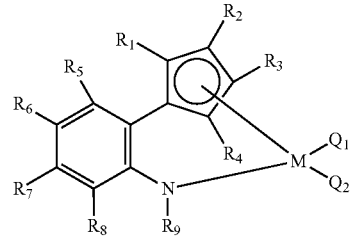

wherein
$R_0$ is a protecting group;
$R_1$, $R_2$, $R_3$, and $R_4$ are each independently a hydrogen atom; a silyl radical; an alkyl radical having 1 to 20 carbon atoms or an aryl radical having 5 to 20 carbon atoms; an alkenyl radical having 2 to 20 carbon atoms, an alkylaryl radical having 6 to 20 carbon atoms, or an arylalkyl radical having 6 to 20 carbon atoms; or a metalloid radical of a metal belonging to Group 14 substituted with a hydrocarbyl having 1 to 20 carbon atoms; at least two of $R_1$, $R_2$, $R_3$, and $R_4$ may be connected to each other to form an aliphatic ring having 5 to 20 carbon atoms or an aromatic ring having 5 to 20 carbon atoms; at least two of $R_1$, $R_2$, $R_3$, and $R_4$ may be connected to each other by an alkylidine radical having 1 to 20 carbon atoms, containing an alkyl radical having 1 to 20 carbon atoms or an aryl radical having 5 to 20 carbon atoms to form a ring;

$R_5$, $R_6$, $R_7$, and $R_8$ are each independently a hydrogen atom; a halogen radical; or an alkyl radical having 1 to 20 carbon atoms or an aryl radical having 5 to 20 carbon atoms; and at least two of $R_5$, $R_6$, $R_7$, and $R_8$ may be connected to each other to form an aliphatic ring having 5 to 20 carbon atoms or an aromatic ring having 5 to 20 carbon atoms;

$R_9$ is a hydrogen atom; a branched, linear, or cyclic alkyl radical having 1 to 20 carbon atoms; or an aryl radical having 5 to 20 carbon atoms; and $R_9$ and $R_8$ may be connected to each other to form an N-containing, substituted or unsubstituted, aliphatic ring having 5 to 20 carbon atoms or aromatic ring having 5 to 20 carbon atoms;

M is a transition metal belonging to Group 4; and $Q_1$ and $Q_2$ are each independently a halogen radical; an alkylamido radical having 1 to 20 carbon atoms, or an arylamido radical having 5 to 20 carbon atoms; an alkyl radical having 1 to 20 carbon atoms, an alkenyl radical having 2 to 20 carbon atoms, an aryl radical having 5 to 20 carbon atoms, an alkylaryl radical having 6 to 20 carbon atoms, or an arylalkyl radical having 6 to 20 carbon atoms; or an alkylidene radical having 1 to 20 carbon atoms.

According to one embodiment of the present invention, in the method for preparing a transition metal complex, as the compound containing a protecting group, trimethylsilyl chloride, benzyl chloride, t-butoxycarbonyl chloride, benzyloxycarbonyl chloride, carbon dioxide, and the like are preferred.

According to another embodiment of the present invention, in the method for preparing a transition metal complex, if the compound containing a protecting group is carbon dioxide, the compound represented by Formula 2 is preferably a lithium carbamate compound represented by Formula 2a below:

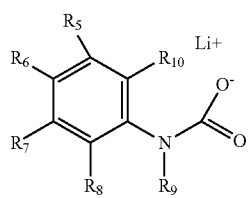

<Formula 2a> wherein $R_5$, $R_6$, $R_7$, $R_8$, $R_9$, and $R_{10}$ are as defined above.

According to a still another embodiment of the present invention, in the method for preparing a transition metal complex, the transition metal complex represented by Formula 6 is preferably represented by Formula 7, Formula 8, or Formula 9, as shown below:

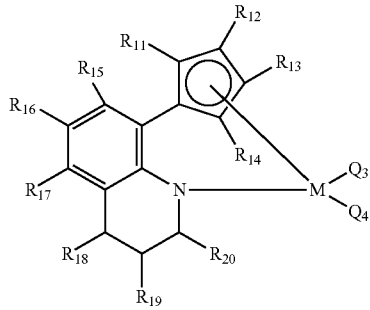

<Formula 7>

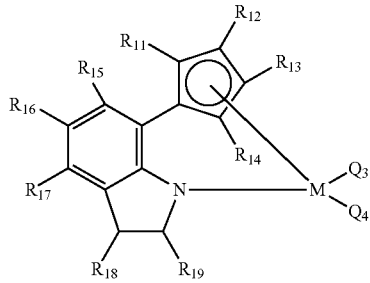

<Formula 8>

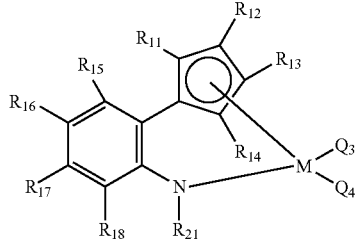

<Formula 9> wherein
$R_{11}$, $R_{12}$, $R_{13}$, and $R_{14}$ are each independently a hydrogen atom; an alkyl radical having 1 to 20 carbon atoms or an aryl radical having 5 to 20 carbon atoms; an alkenyl radical having 2 to 20 carbon atoms, an alkylaryl radical having 6 to 20 carbon atoms, or an arylalkyl radical having 6 to 20 carbon atoms; or a metalloid radical of a metal belonging to Group 14 substituted with hydrocarbyl having 1 to 20 carbon atoms; and at least two) of $R_{11}$, $R_{12}$, $R_{13}$, and $R_{14}$ may be connected to each other to form an aliphatic ring having 5 to 20 carbon atoms or an aromatic ring having 5 to 20 carbon atoms;

$R_{15}$, $R_{16}$, $R_{17}$, $R_{18}$, $R_{19}$, and $R_{20}$ are each independently a hydrogen atom; a halogen radical; an alkyl radical having 1 to 20 carbon atoms or an aryl radical having 5 to 20 carbon atoms; and at least to of $R_{15}$, $R_{16}$, $R_{17}$, $R_{18}$, $R_{19}$, and $R_{20}$ may be connected to each other to form an aliphatic ring having 5 to 20 carbon atoms or an aromatic ring having 5 to 20 carbon atoms;

$R_{21}$ is a hydrogen atom; a branched, linear, or cyclic alkyl radical having 1 to 20 carbon atoms; or an aryl radical having 5 to 20 carbon atoms;

M is a transition metal belonging to Group 4; and $Q_3$ and $Q_4$ are each independently a halogen radical; an alkylamido radical having 1 to 20 carbon atoms or an arylamido radical having 5 to 20 carbon atoms; or an alkyl radical having 1 to 20 carbon atoms.

According to a still another embodiment of the present invention, in the method for preparing a transition metal complex, the transition metal complex represented by Formula 6 is preferably represented by one of the structural formulae as shown below:

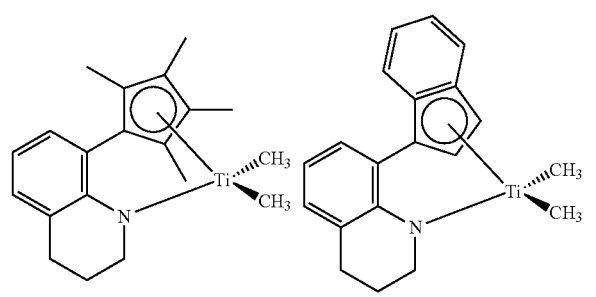
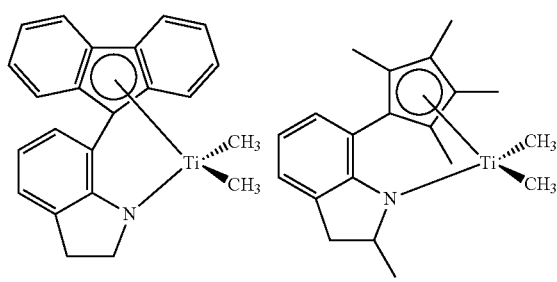
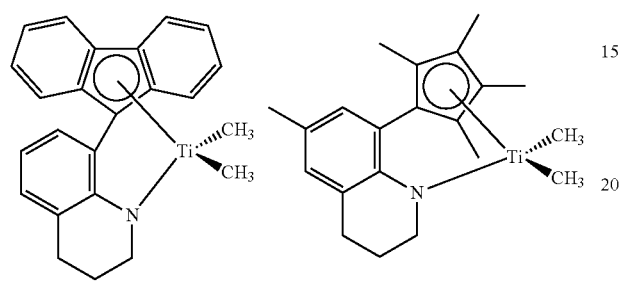
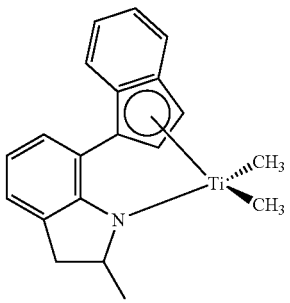
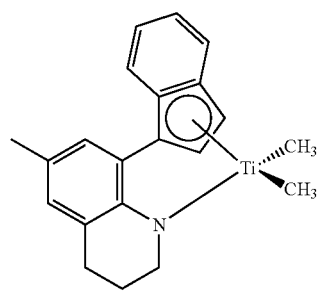
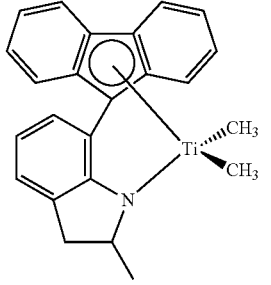
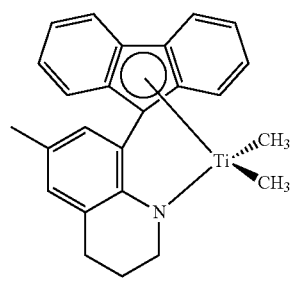
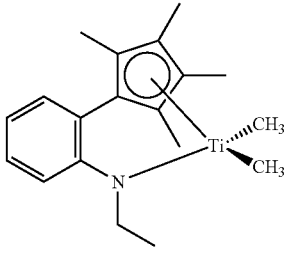
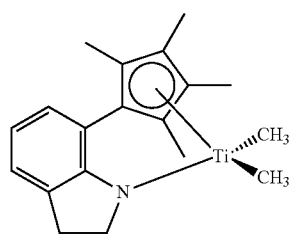
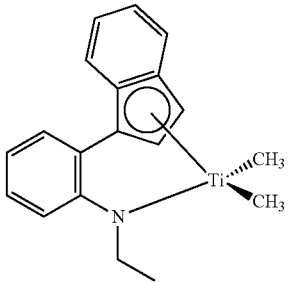
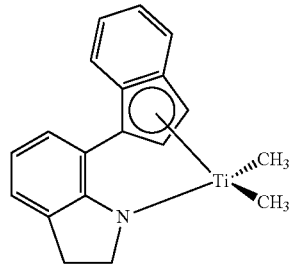
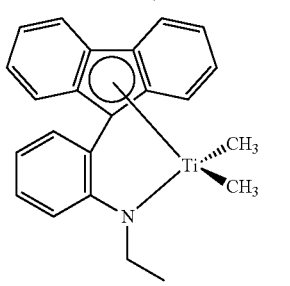

-continued

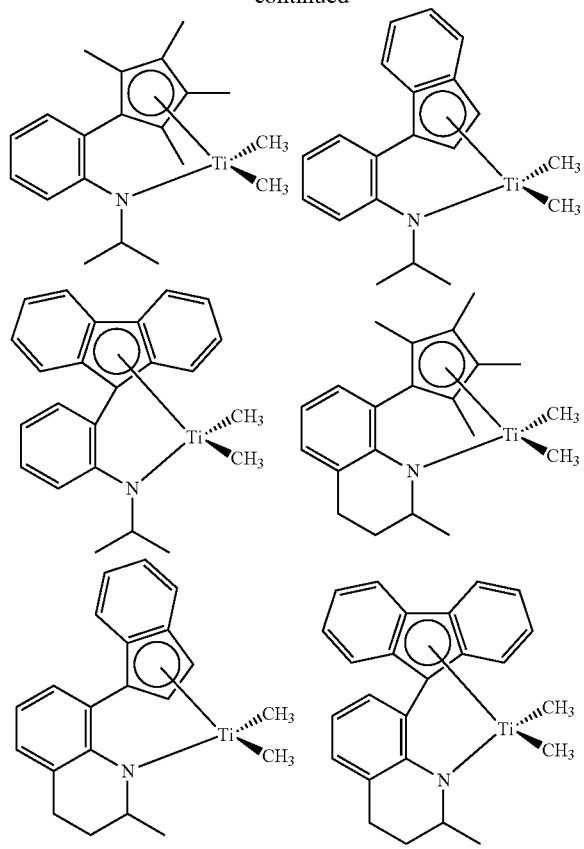

According to a second aspect of the present invention, there is provided a transition metal complex represented by Formula 6 below:

<Formula 6>

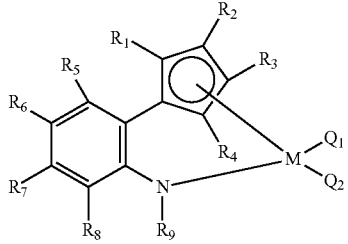

wherein $R_1$, $R_2$, $R_3$, and $R_4$ are each independently a hydrogen atom; a silyl radical; an alkyl radical having 1 to 20 carbon atoms or an aryl radical having 5 to 20 carbon atoms; an alkenyl radical having 2 to 20 carbon atoms, an alkylaryl radical having 6 to 20 carbon atoms, or an arylalkyl radical having 6 to 20 carbon atoms; or a metalloid radical of a metal belonging to Group 14 substituted with hydrocarbyl having 1 to 20 carbon atoms; at least two of $R_1$, $R_2$, $R_3$, and $R_4$ may be connected to each other to form an aliphatic ring having 5 to 20 carbon atoms or an aromatic ring having 5 to 20 carbon atom; and at least two of $R_1$, $R_2$, $R_3$, and $R_4$ may be connected to each other by an alkylidine radical having 1 to 20 carbon atoms, containing an alkyl radical having 1 to 20 carbon atoms or an aryl radical having 5 to 20 carbon atoms to form a ring;

$R_5$, $R_6$, $R_7$, and $R_8$ are each independently a hydrogen atom; a halogen radical; an alkyl radical having 1 to 20 carbon atoms or an aryl radical having 5 to 20 carbon atoms; and at least two of $R_5$, $R_6$, $R_7$ and $R_8$ may be connected to each other to form an aliphatic ring having 5 to 20 carbon atoms or an aromatic ring having 5 to 20 carbon atoms;

$R_9$ is a hydrogen atom; a branched, linear, or cyclic alkyl radical having 1 to 20 carbon atoms; or an aryl radical having 5 to 20 carbon atoms; $R_9$ and $R_8$ may be connected to each other to form an N-containing, substituted or unsubstituted, aliphatic ring having 5 to 20 carbon atoms or aromatic ring having 5 to 20 carbon atoms;

M is a transition metal belonging to Group 4; and $Q_1$ and $Q_2$ are each independently a halogen radical; an alkylamido radical having 1 to 20 carbon atoms, or an arylamido radical having 5 to 20 carbon atoms; an alkyl radical having 1 to 20 carbon atoms, an alkenyl radical having 2 to 20 carbon atoms, an aryl radical having 5 to 20 carbon atoms, an alkylaryl radical having 6 to 20 carbon atoms, or an arylalkyl radical having 6 to 20 carbon atoms; or an alkylidene radical having 1 to 20 carbon atoms.

According to one embodiment of the present invention, the transition metal complex represented by Formula 6 is preferably represented by one of Formulae 7, 8, and 9 below:

<Formula 7>

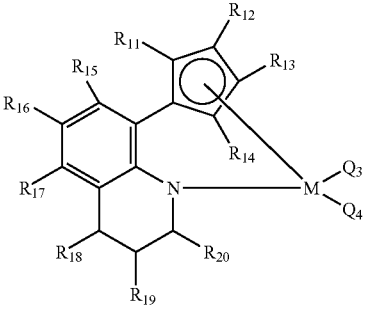

<Formula 8>

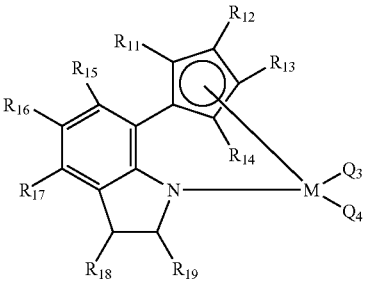

<Formula 9>

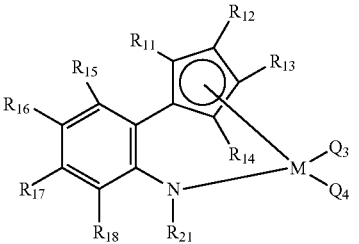

wherein $R_{11}$, $R_{12}$, $R_{13}$, and $R_{14}$ are each independently a hydrogen atom; a silyl radical; an alkyl radical having 1 to 20 carbon atoms or an aryl radical having 5 to 20 carbon atoms; an alkenyl radical having 2 to 20 carbon atoms, an alkylaryl radical having 6 to 20 carbon atoms, or an arylalkyl radical having 6 to 20 carbon atoms; or a metalloid radical of a metal belonging to Group 14 substituted with hydrocarbyl having 1 to 20 carbon atoms; and at least two of $R_{11}$, $R_{12}$, $R_{13}$ and $R_{14}$ may be connected to each other to form an aliphatic ring having 5 to 20 carbon atoms or an aromatic ring having 5 to 20 carbon atoms;

$R_{15}$, $R_{16}$, $R_{17}$, $R_{18}$, $R_{19}$ and $R_{20}$ are each independently a hydrogen atom; a halogen radical; an alkyl radical having 1 to 20 carbon atoms or an aryl radical having 5 to 20 carbon atoms; and at least two of $R_{15}$, $R_{16}$, $R_{17}$, $R_{18}$, $R_{19}$ and $R_{20}$ may be connected to each other to form an aliphatic ring having 5 to 20 carbon atoms or an aromatic ring having 5 to 20 carbon atoms;

$R_{21}$ is a hydrogen atom; a branched, linear, or cyclic alkyl radical having 1 to 20 carbon atoms; or an aryl radical having 5 to 20 carbon atoms;

$Q_3$ and $Q_4$ are each independently a halogen radical; an alkylamido radical having 1 to 20 carbon atoms or an arylamido radical having 5 to 20 carbon atoms; or an alkyl radical having 1 to 20 carbon atoms; and M is a transition metal belonging to Group 4.

According to another embodiment of the present invention, the transition metal complex represented by Formula 6 is represented by one of the structural formulae as shown below:

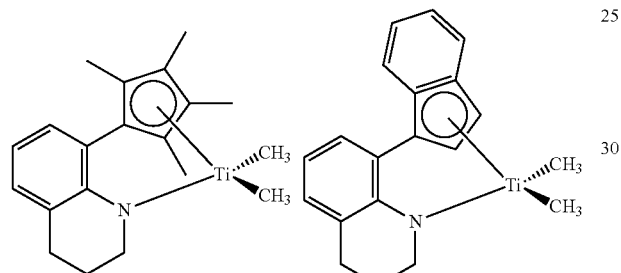

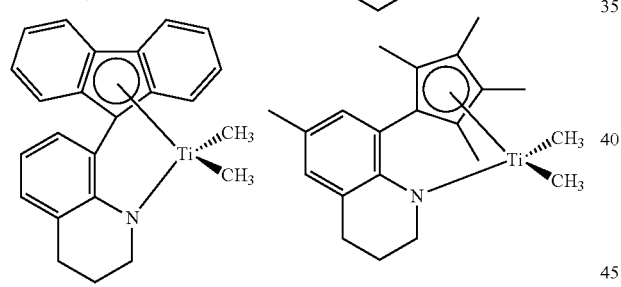

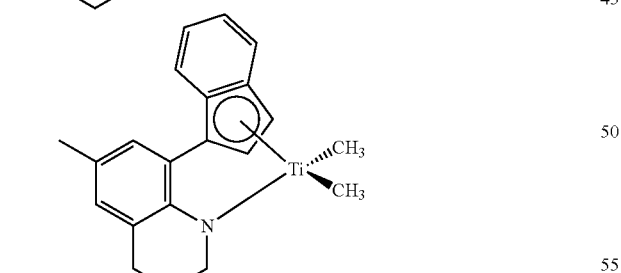

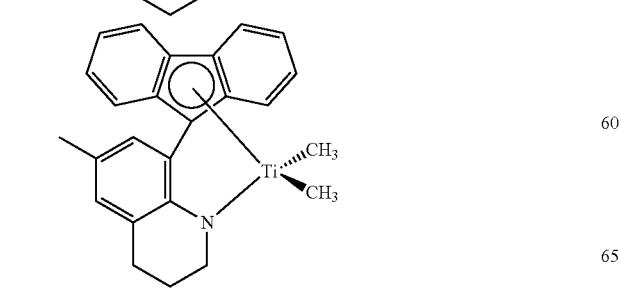

-continued

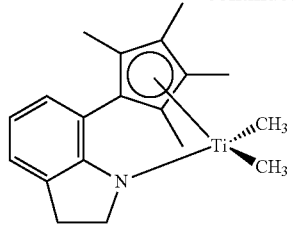

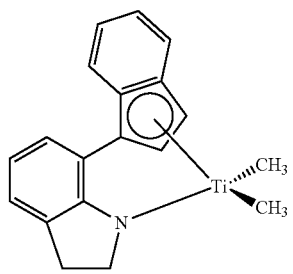

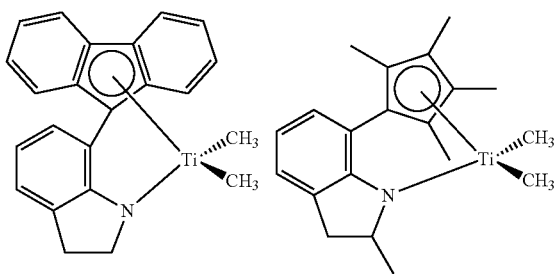

-continued

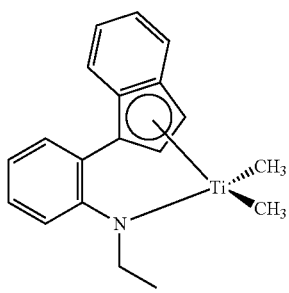

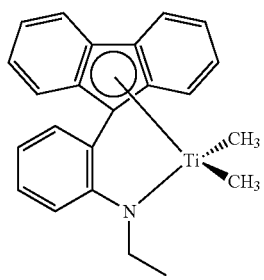

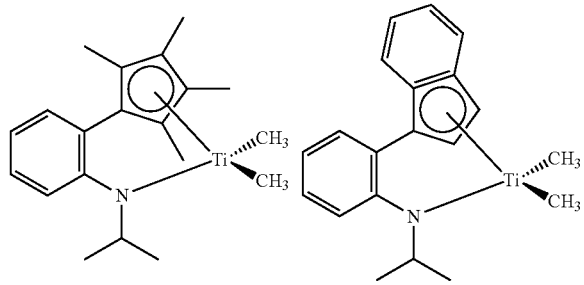

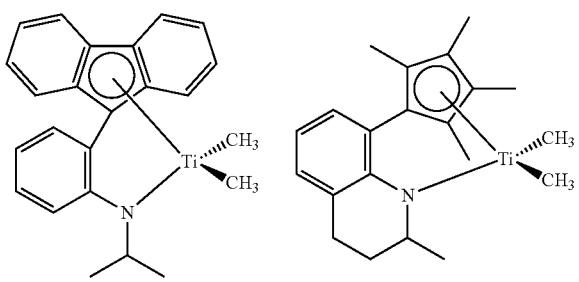

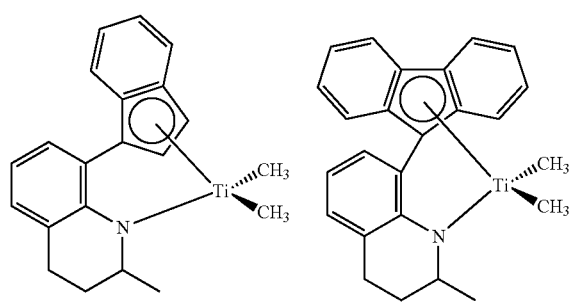

Furthermore, according to the second aspect of the present invention, there is provided an amine-based compound represented by Formula 4 below:

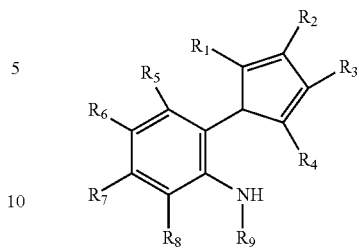

<Formula 4> wherein $R_1$, $R_2$, $R_3$, $R_4$, $R_5$, $R_6$, $R_7$, $R_8$, and $R_9$ are as defined above.

According to a third aspect of the present invention, there is provided a catalyst composition comprising:

a transition metal complex represented by Formula 6 below; and at least one cocatalyst compound selected from the group consisting of the compounds represented by Formulae 10, 11, and 12 below:

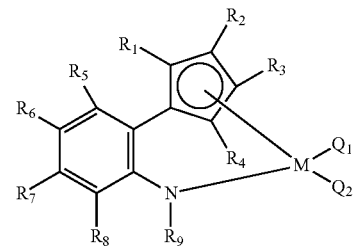

<Formula 6> wherein $R_1$, $R_2$, $R_3$, $R_4$, $R_5$, $R_6$, $R_7$, $R_8$, $R_9$, $Q_1$, and $Q_2$ are as defined above.

$$-[Al(R_{22})-O]_a \qquad \text{<Formula 10>}$$

wherein $R_{22}$'s are each independently a halogen radical; a hydrocarbyl radical having 1 to 20 carbon atoms; or a hydrocarbyl radical having 1 to 20 carbon atoms substituted with halogen; and a is an integer of no less than 2;

$$D(R_{22})_3 \qquad \text{<Formula 11>}$$

wherein D is aluminum or boron; and $R_{22}$'s are each independently as defined above;

$$[L-H]^+[Z(A)_4]^- \text{ or } [L]^+[Z(A)_4]^- \qquad \text{<Formula 12>}$$

wherein L is a neutral or cationic Lewis acid; H is a hydrogen atom; Z is an element belonging to Group 13; A's are each independently an aryl radial having 6 to 20 carbon atoms or alkyl radical having 1 to 20 carbon atoms, substituted with one or more hydrogen atoms; and the substituent is a halogen, a hydrocarbyl radical having 1 to 20 carbon atoms, an alkoxy radical having 1 to 20 carbon atoms, or an aryloxy radical having 6 to 20 carbon atoms.

According to one embodiment of the present invention, in the catalyst composition, the transition metal complex represented by Formula 6 is preferably represented by Formula 7, Formula 8, or Formula 9, as shown below:

<Formula 7>
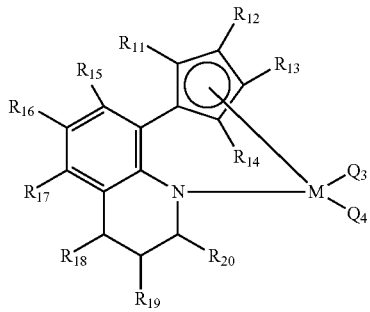
<Formula 8>
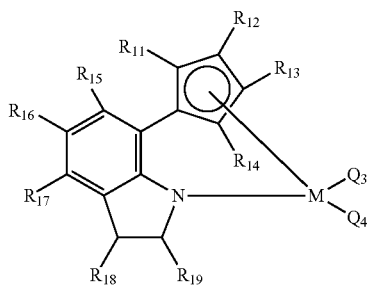
<Formula 9>
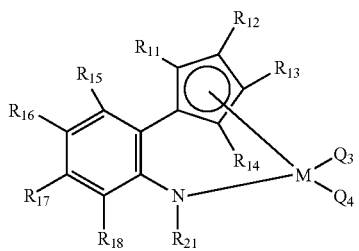
wherein $R_{11}$, $R_{12}$, $R_{13}$, $R_{14}$, $R_{15}$, $R_{16}$, $R_{17}$, $R_{18}$, $R_{19}$, $R_{20}$, $R_{21}$, $Q_3$, and $Q_4$ are as defined above.
According to another embodiment of the present invention, in the catalyst composition, the transition metal complex represented by Formula 6 is preferably represented by one of the structural formulae as shown below:
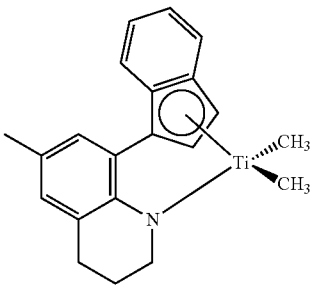
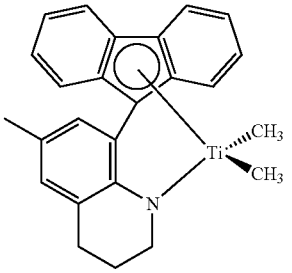
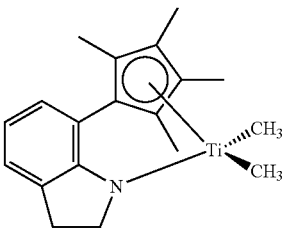
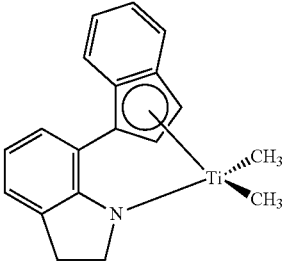
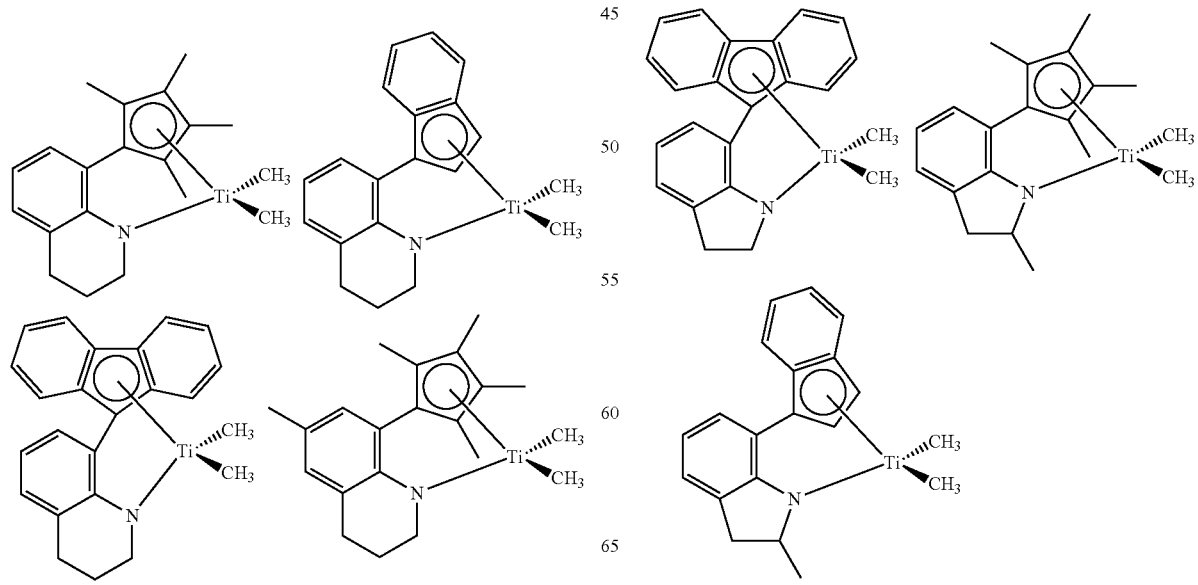

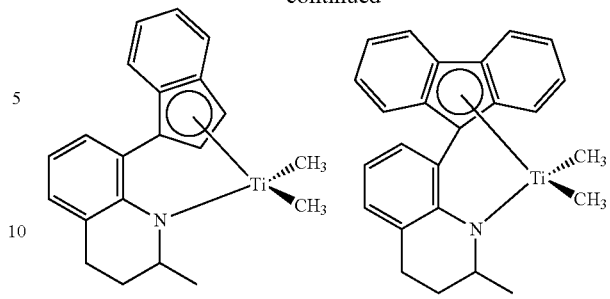

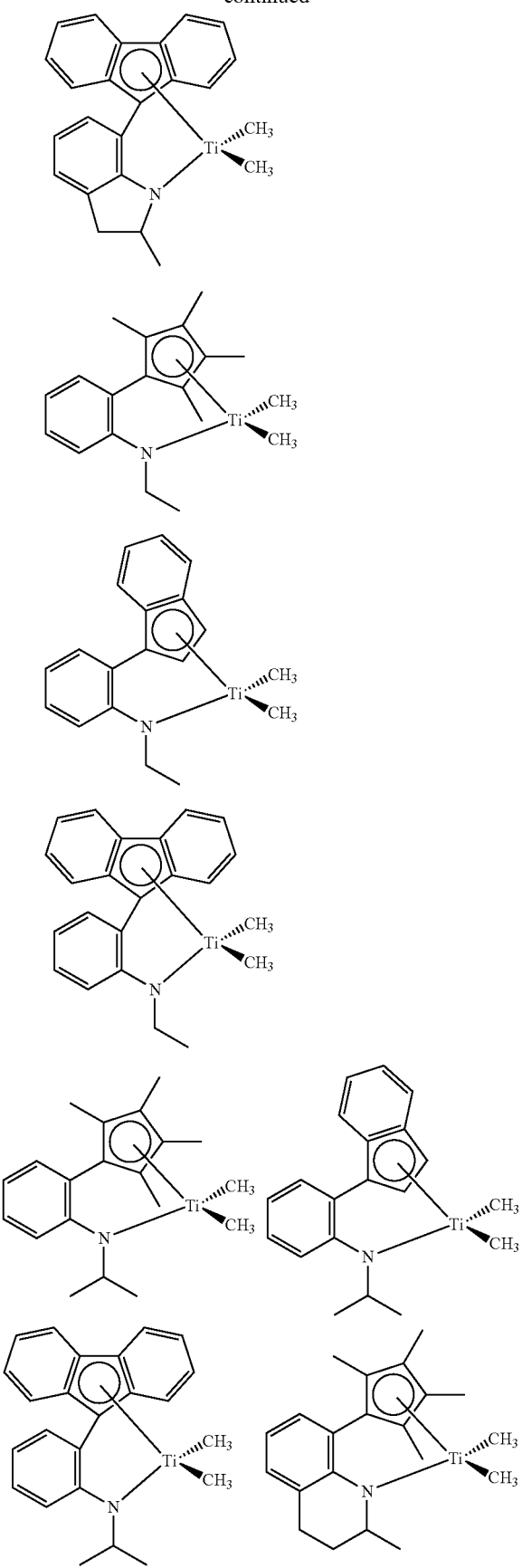

According to another embodiment of the present invention, in the catalyst composition, the molar ratio of the transition metal complex represented by Formula 6 to the compound represented by Formula 10 or 11 is preferably 1:2 to 1:5000, and the molar ratio of the transition metal complex represented by Formula 6 to the compound represented by Formula 12 is preferably 1:1 to 1:25.

As compared with a conventional method for preparing a transition metal complex using boronic acid, etc., the method for preparing a transition metal complex according to the present invention comprises a step of blocking a by-reaction of a nitrogen atom using a compound containing a protecting group, and thus it is possible to prepare a transition metal complex in a simpler manner in a high yield.

Advantageous Effects

The method for preparing a transition metal complex according to the present invention comprises a step of blocking a by-reaction of a nitrogen atom using a compound containing a protecting group, and thus it is possible to prepare a transition metal complex in a simpler manner in a high yield.

Furthermore, the transition metal complex according to the present invention has a pentagon ring structure having an amido group connected by a phenylene bridge in which a stable bond is formed in the vicinity of a metal site, and thus, sterically monomers can easily approach the transition metal complex.

When a catalyst composition comprising the transition metal complex is applied in copolymerization of ethylene and monomers having large steric hindrance, a very low density polyolefin copolymer having a density of less than 0.910 g/cc, in addition to a polyolefin having a high molecular weight and a linear low density, can be prepared. Furthermore, the reactivity is also very high.

BEST MODE FOR CARRYING OUT THE INVENTION

Hereinafter, the present invention will be described in detail.

According to a first aspect of the present invention, the invention provides a method for preparing a transition metal complex, comprising the steps of:

(a) reacting an amine-based compound represented by Formula 1 below with an alkyl lithium and then adding a compound containing a protecting group (—$R_0$) thereto to prepare a compound represented by Formula 2 below;

(b) reacting the compound represented by Formula 2 with an alkyl lithium, and adding a ketone-based compound represented by Formula 3 below to prepare an amine-based compound represented by Formula 4 below;

(c) reacting the compound represented by Formula 4 with n-butyl lithium to prepare a dilithium compound represented by Formula 5 below; and (d) reacting the compound represented by Formula 5 with MCl₄ (M=Ti, Zr, or Hf) and an organic lithium compound to prepare a transition metal complex represented by Formula 6 below:

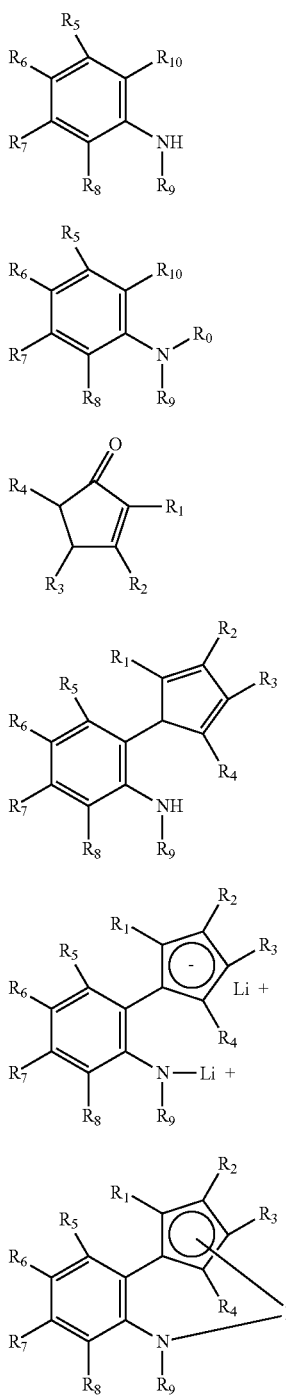

<Formula 1>

<Formula 2>

<Formula 3>

<Formula 4>

<Formula 5>

<Formula 6> wherein $R_0$, $R_1$, $R_2$, $R_3$, $R_4$, $R_5$, $R_6$, $R_7$, $R_8$, $R_9$, M, $Q_1$ and $Q_2$ are as defined above.

In the method for preparing a transition metal complex, a protecting group for a nitrogen atom is introduced to the amine compound represented by Formula 1, and then a cyclo-cyclopentadienyl group is introduced. Thereafter, the protect-ing group introduced to the nitrogen atom is removed, thereby preparing a transition metal complex.

As the compound containing a protecting group, trimethylsilyl chloride, benzyl chloride, t-butoxycarbonyl chloride, benzyloxycarbonyl chloride, carbon dioxide, and the like are preferred.

Thus, as the protecting group, a trimethylsilyl group, a benzyl group, a t-butoxycarbonyl group, a benzyloxycarbonyl group, —C(=O)O⁻, and the like are preferred.

Particularly, if the compound containing a protecting group is carbon dioxide, the compound represented by Formula 2 is a lithium carbamate compound represented by Formula 2a below:

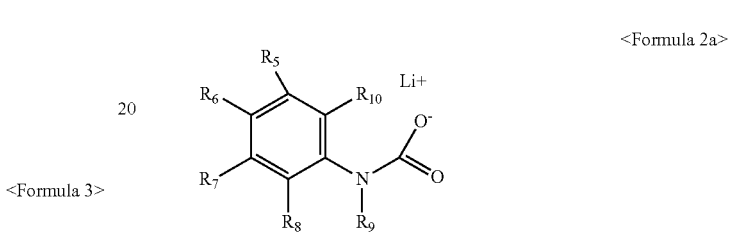

<Formula 2a> wherein $R_5$, $R_6$, $R_7$, $R_8$, $R_9$, and $R_{10}$ are as defined above.

Carbon dioxide can be easily removed from the lithium carbamate compound by controlling the temperature. Accordingly, in the preparation method in which carbon dioxide is introduced for the preparation of the transition metal complex represented by Formula 1, a transition metal complex can be prepared in a simple and efficient manner in a high yield without any by-reaction of a nitrogen atom present in the reactants.

In the method for preparing a transition metal complex, the transition metal complex represented by Formula 6 is preferably represented by Formula 7, Formula 8, or Formula 9, as shown below:

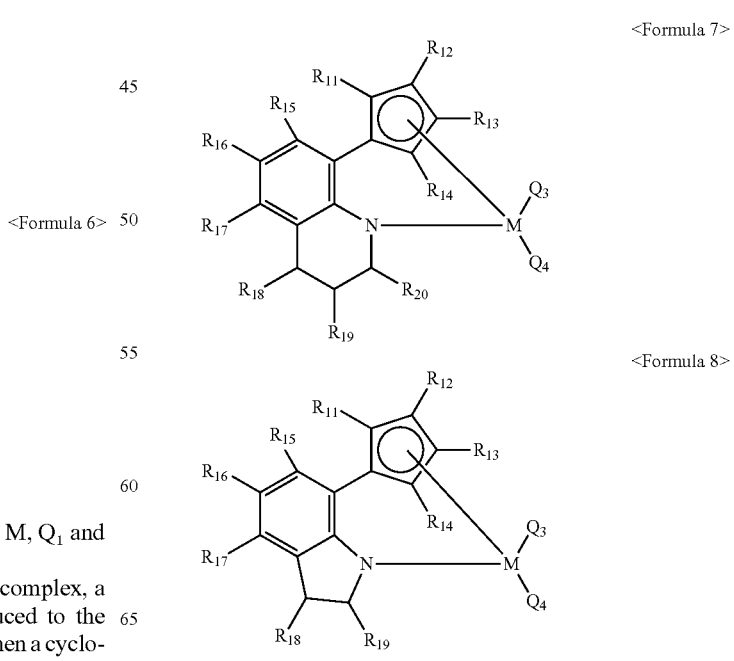

<Formula 7>

<Formula 8>

<Formula 9>
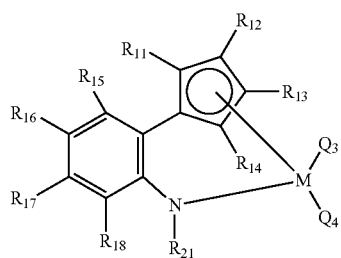
wherein $R_{11}$, $R_{12}$, $R_{13}$, $R_{14}$, $R_{15}$, $R_{16}$, $R_{17}$, $R_{18}$, $R_{19}$, $R_{20}$, $R_{21}$, M, $Q_3$, and $Q_4$ are as defined above.
Furthermore, in the method for preparing a transition metal complex, the transition metal complex represented by Formula 6 is more preferably represented by one of the structural formulae as shown below:
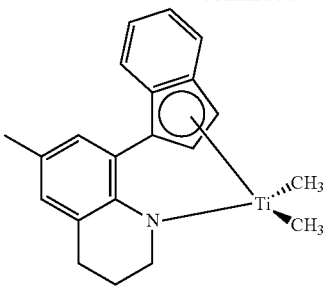
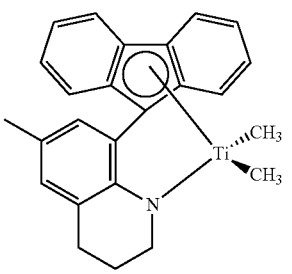
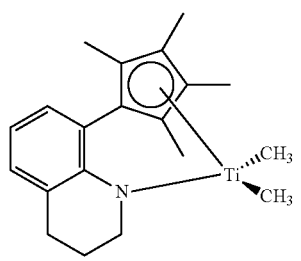
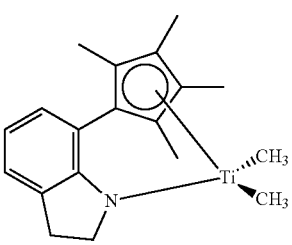
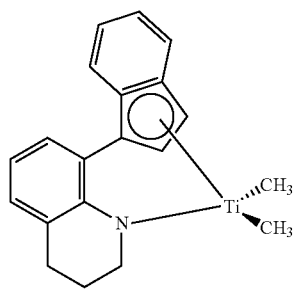
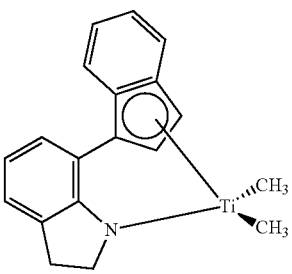
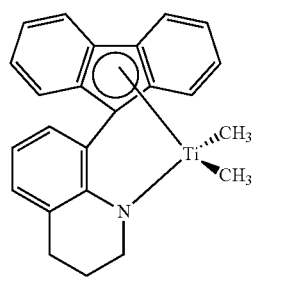
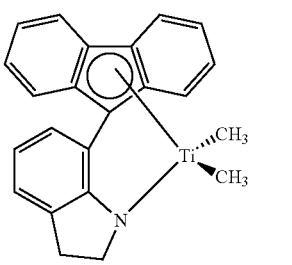
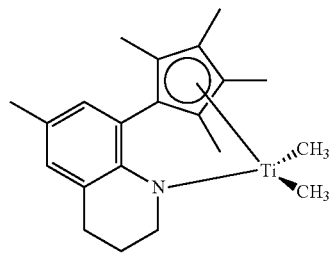
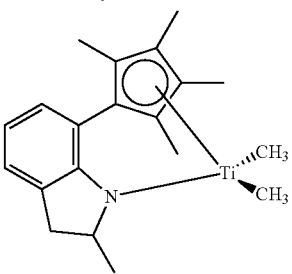

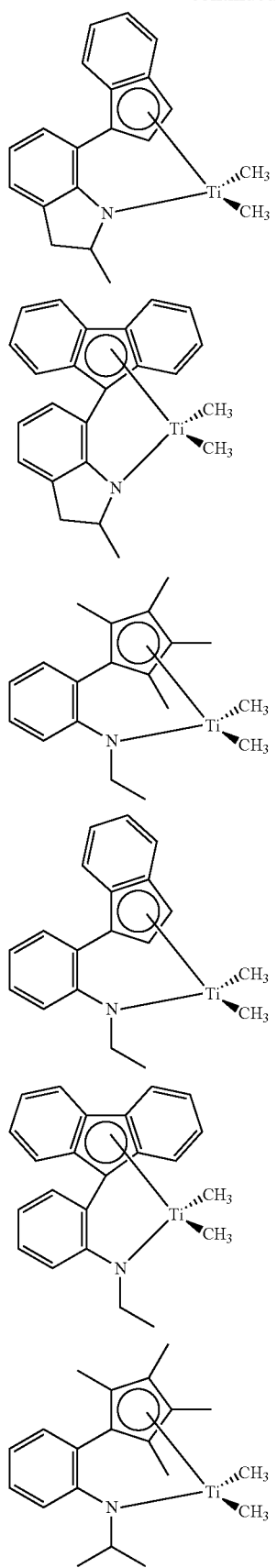
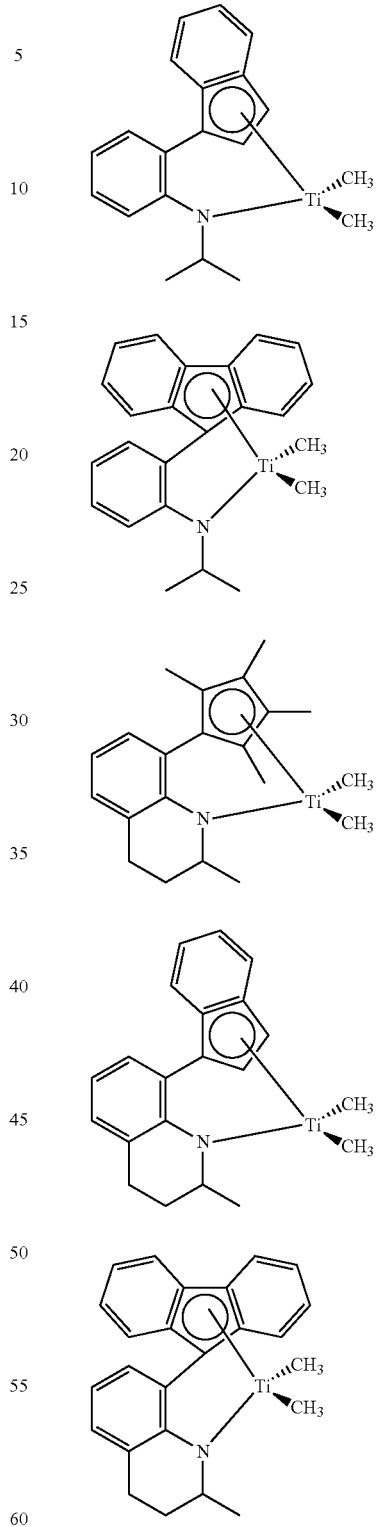
One embodiment of the specific method for preparing the compound as above can be shown in Reaction Schemes 1 and 2 below:

<Reaction Scheme 1>

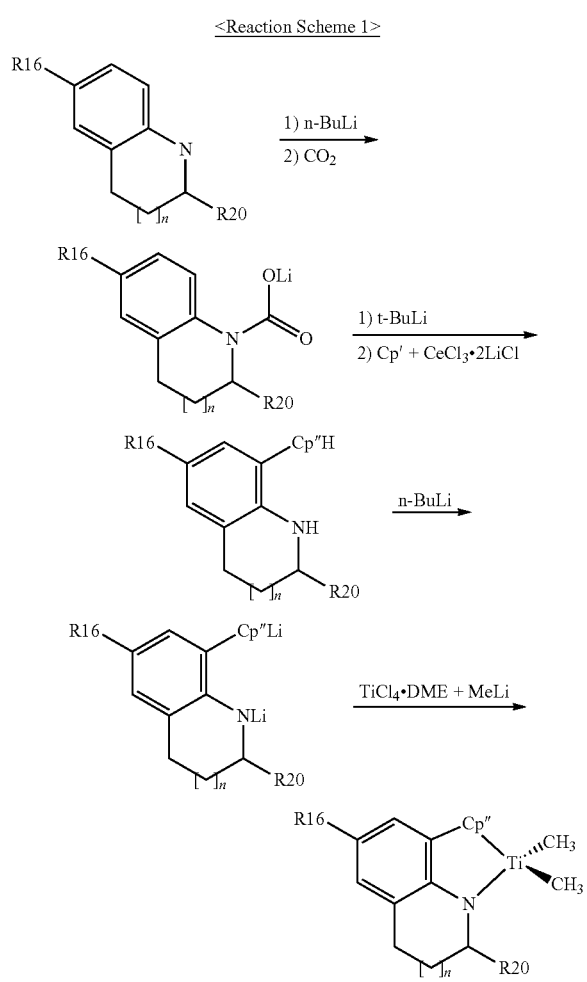

In Reaction Scheme 1, R16 and R20 are each preferably hydrogen, methyl, or the like, Cp' is preferably tetramethylcyclopentanone, indenone, fluorenone, or the like, Cp" is preferably tetramethylcyclopenta-dienyl, indenyl, fluorenyl, or the like, and n is 0 or 1.

<Reaction Scheme 2>

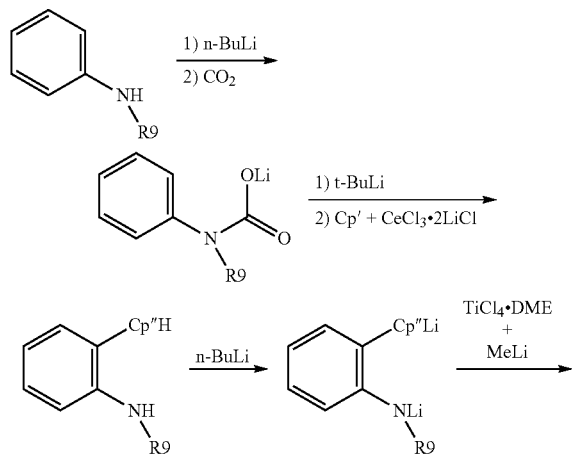

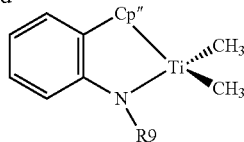

In Reaction Scheme 2, R3 is preferably ethyl, isopropyl, or the like, Cp' is tetramethylcyclopentanone, indenone, fluorenone, or the like, and Cp" is tetramethylcyclopenta-dienyl, indenyl, fluorenyl, or the like.

Details on Reaction Schemes as above are provided in Examples.

According to a second aspect of the present invention, the invention provides a transition metal complex represented by Formula 6 below:

<Formula 6>

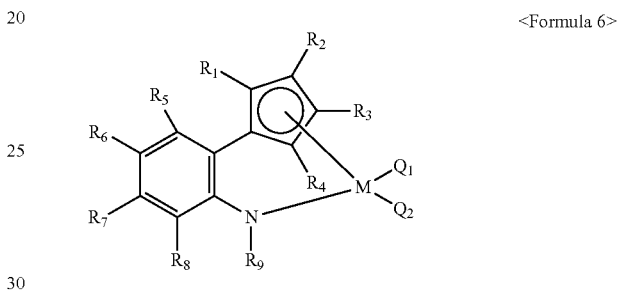

wherein $R_1$, $R_2$, $R_3$, $R_4$, $R_5$, $R_6$, $R_7$, $R_8$, $R_9$, M, $Q_1$, and $Q_2$ are as defined above.

A metal site of the transition metal complex represented by Formula 6 is connected by a cyclopentadienyl ligand which is connected to a phenylene bridge to which a ring shaped amido group is introduced. Thus, its structural inherence gives characteristics that the angle of Cp-M-N structure is narrow, and a wide angle is maintained in the $Q_1$-M-$Q_2$ structure to which a monomer approaches. In addition, as compared to a CGC structure that includes a silicon bridge for connection, the transition metal complex represented by Formula 6 has a structure in which Cp, a phenylene bridge, nitrogen, and a metal site are connected in this order to form a stable and strong pentagon ring. Accordingly, when the complex compound which is activated by the reaction with a cocatalyst such as methylaluminoxane and $B(C_6F_5)_3$, is then applied in olefin polymerization, a polyolefin which is characterized by a high activity, a high molecular weight, a high degree of copolymerization, and the like, can be obtained even at a high polymerization temperature. In particular, a very low density polyolefin copolymer having a density of less than 0.910 g/cc, in addition to a linear, low density polyethylene having a density of about 0.910 to 0.930 g/cc, can also be prepared since the structure of the catalyst allows a great mount of α-olefin to be introduced. Various substituents can be introduced into a cyclopentadienyl ring and a quinoline-based ring. As a consequence, the structures, properties, etc. of the resulting polyolefin can be controlled since electronic and steric environments in the vicinity of the metal can be easily regulated. The complex according to the present invention may be preferably used to prepare a catalyst for polymerization of olefin monomers. However, use of the complex is not limited thereto, and the complex can be applied in any other field where the transition metal complex can be used Specifically, as the transition metal complex represented by Formula 6, preferred is a transition metal complex having a structure represented by Formula 7, 8, or 9 below, which can control electronic and steric environments in the vicinity of metal:

<Formula 7>

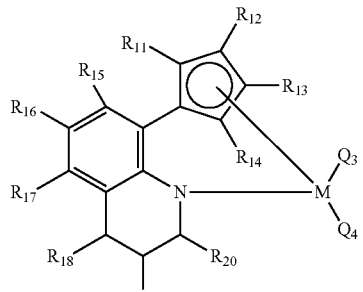

<Formula 8>

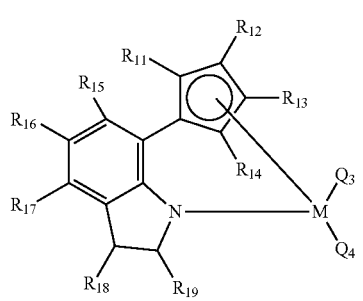

<Formula 9>

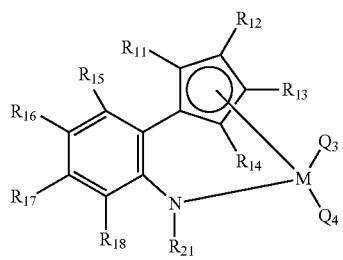

wherein $R_{11}$, $R_{12}$, $R_{13}$, $R_{14}$, $R_{15}$, $R_{16}$, $R_{17}$, $R_{18}$, $R_{19}$, $R_{20}$, $R_{21}$, M, $Q_3$, and $Q_4$ are as defined above.

Furthermore, as the transition metal complex represented by Formula 6, further preferred is a complex represented by one of the structural formulae below:

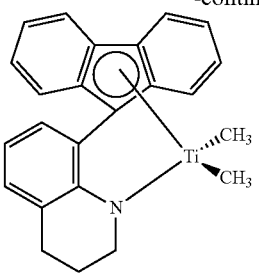

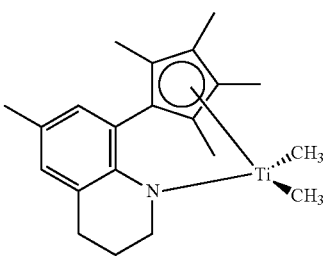

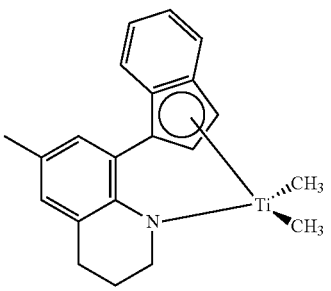

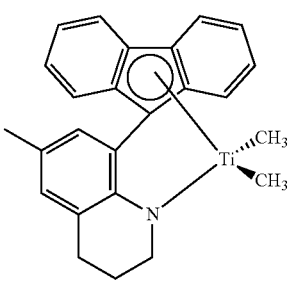

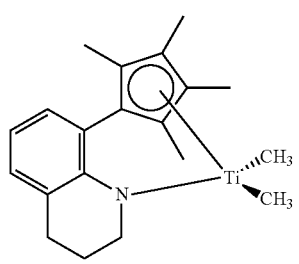

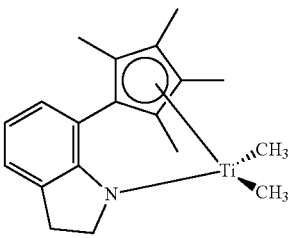

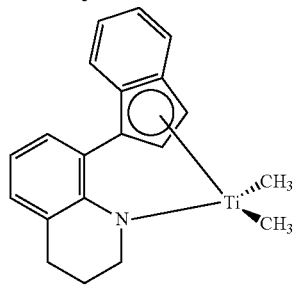

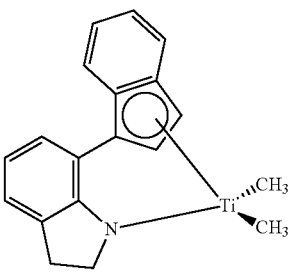

29
-continued
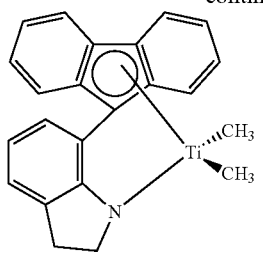
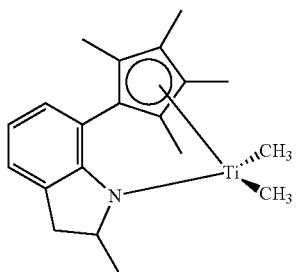
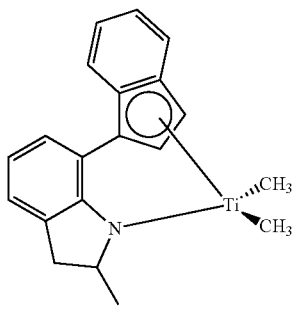
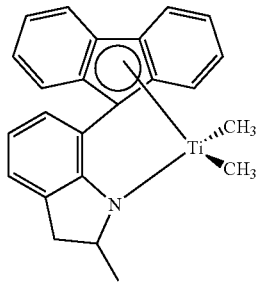
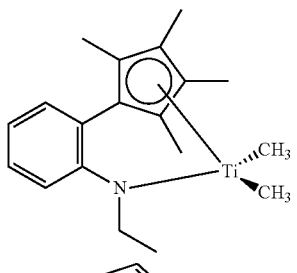
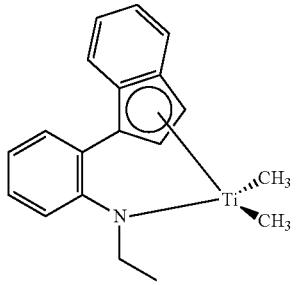
30
-continued
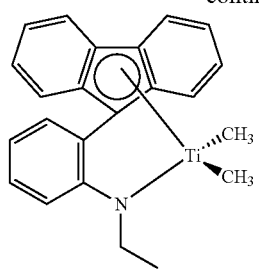
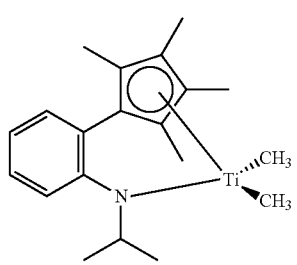
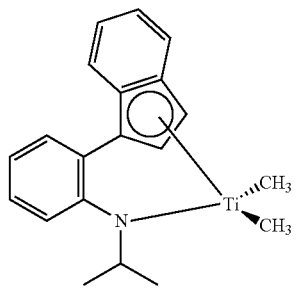
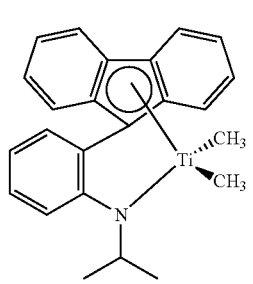
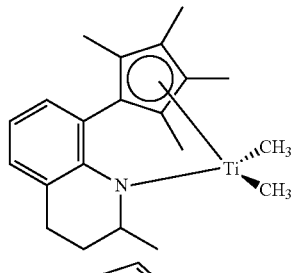
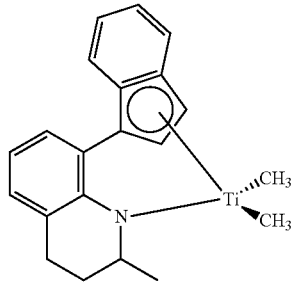

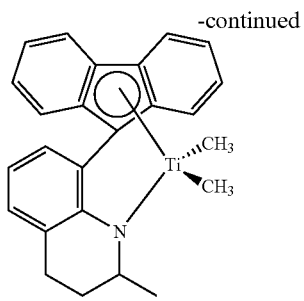

Moreover, according to the second aspect of the present invention, the invention provides an amine-based compound represented by Formula 4 below:

<Formula 4>

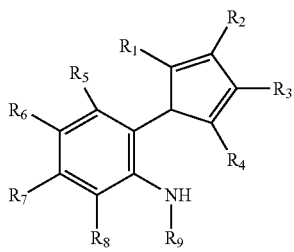

wherein $R_1$, $R_2$, $R_3$, $R_4$, $R_5$, $R_6$, $R_7$, $R_8$, and $R_9$ are as defined above.

The amine-based compound represented by Formula 4 is an intermediate obtained during the preparation of the transition metal complex of the present invention, which can also be used in other fields.

According to a third aspect of the present invention, the invention provides a catalyst composition comprising:
a transition metal complex represented by Formula 6 below; and
at least one cocatalyst compound selected from the group consisting of the compounds represented by Formulae 10, 11, and 12 below:

<Formula 6>

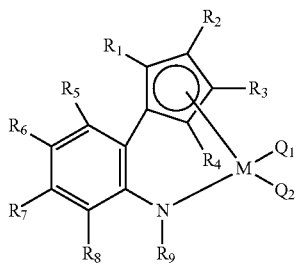

wherein $R_1$, $R_2$, $R_3$, $R_4$, $R_5$, $R_6$, $R_7$, $R_8$, $R_9$, $Q_1$, and $Q_2$ are as defined above.

—[Al($R_{22}$)—O]$_a$—  <Formula 10> wherein $R_{22}$'s are each independently a halogen radical; a hydrocarbyl radical having 1 to 20 carbon atoms; or a hydrocarbyl radical having 1 to 20 carbon atoms substituted with halogen; and a is an integer of no less than 2;

D($R_{22}$)$_3$  <Formula 11> wherein D is aluminum or boron; and $R_{22}$'s are each independently as defined above;

[L-H]$^+$[Z(A)$_4$]$^-$ or [L]$^+$[Z(A)$_4$]$^-$  <Formula 12> wherein L is a neutral or cationic Lewis acid; H is a hydrogen atom; Z is an element belonging to Group 13; A's are each independently an aryl radial having 6 to 20 carbon atoms or alkyl radical having 1 to 20 carbon atoms, substituted with one or more hydrogen atoms; and the substituent is a halogen, a hydrocarbyl radical having 1 to 20 carbon atoms, an alkoxy radical having 1 to 20 carbon atoms, or an aryloxy radical having 6 to 20 carbon Warm The catalyst composition of the present invention can be used in various olefin polymerizations.

In the catalyst composition, the transition metal complex represented by Formula 6 is preferably represented by Formula 7, Formula 8, or Formula 9, as shown below:

<Formula 7>

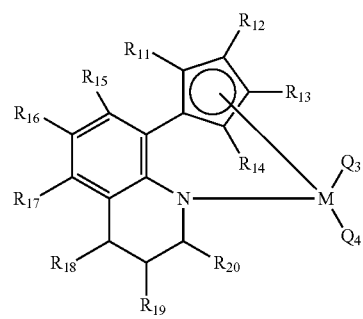

<Formula 8>

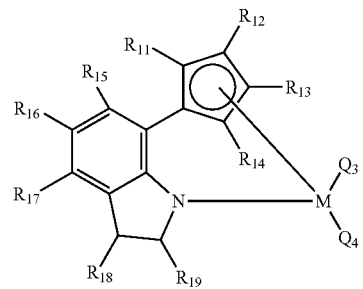

<Formula 9>

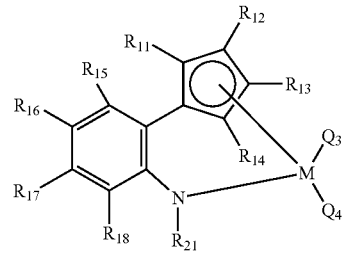

wherein $R_{11}$, $R_{12}$, $R_{13}$, $R_{14}$, $R_{15}$, $R_{16}$, $R_{17}$, $R_{18}$, $R_{19}$, $R_{20}$, $R_{21}$, $Q_3$, and $Q_4$ are as defined above.

More specifically, in the catalyst composition, the transition metal complex represented by Formula 6 is preferably represented by one of the structural formulae as shown below:

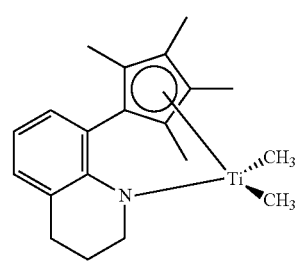

33
-continued
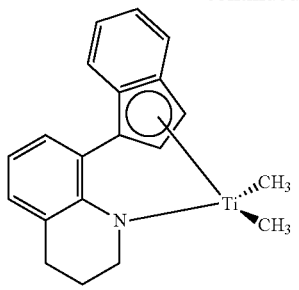
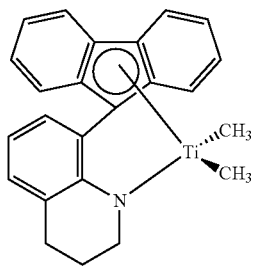
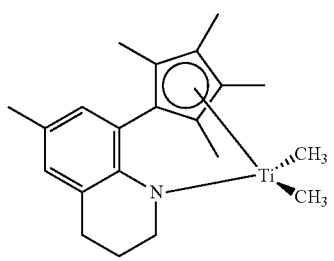
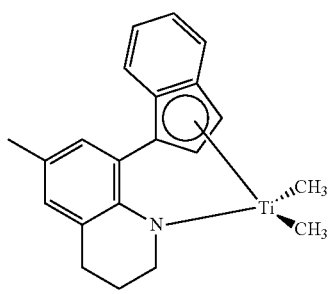
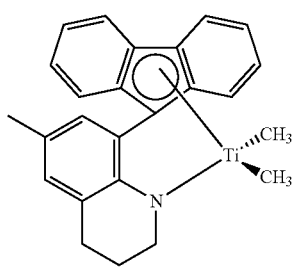
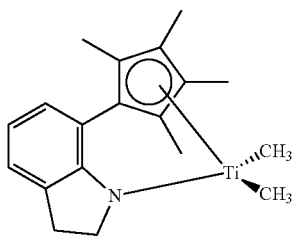
34
-continued
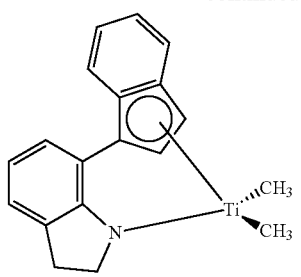
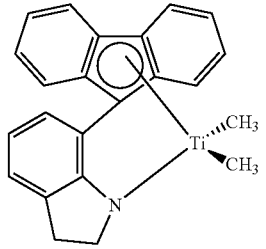
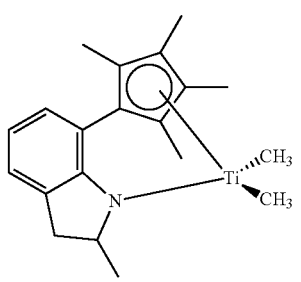
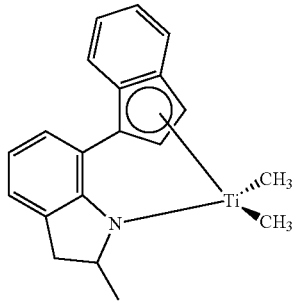
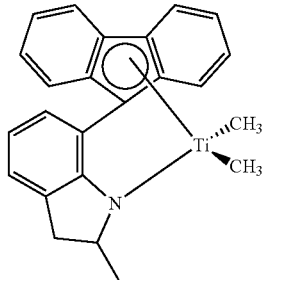
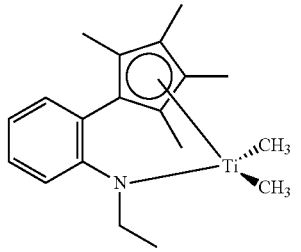

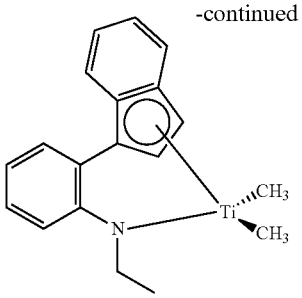

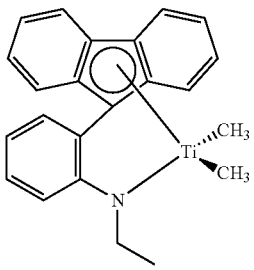

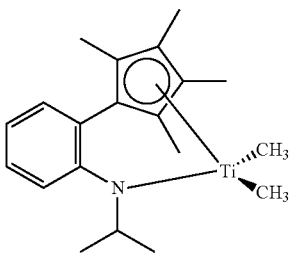

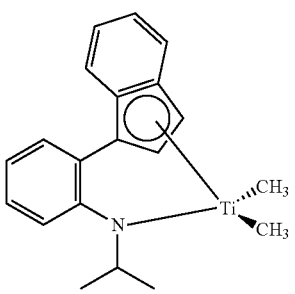

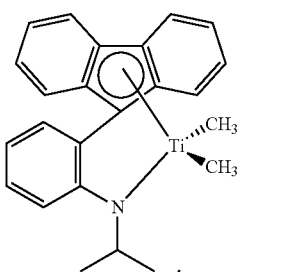

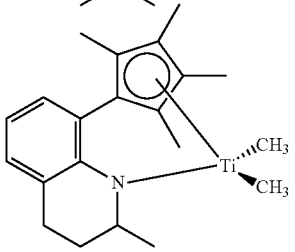

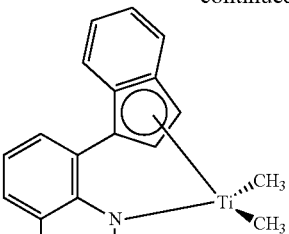

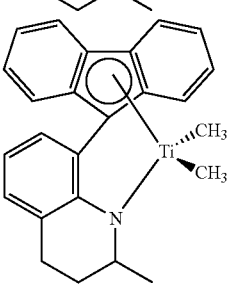

Moreover, the present invention provides a method for preparing the catalyst composition, comprising the steps of:

bringing the transition metal complex represented by Formula 6 into contact with a compound represented by Formula 10 or 11 to obtain a mixture; and adding a compound represented by Formula 12 to the mixture.

The present invention further provides a method for preparing the catalyst composition, comprising the steps of:

bringing the transition metal complex represented by Formula 6 into contact with a compound represented by Formula 12.

In the former method for preparing the catalyst composition, the molar ratio of the transition metal complex represented by Formula 6 to the compound represented by Formula 10 or 11 is preferably 1:2 to 1:5000, more preferably 1:10 to 1:1,000, and must preferably 1:20 to 1:500.

Meanwhile, the molar ratio of the transition metal complex represented by Formula 6 to the compound represented by Formula 12 is preferably 1:1 to 1:25, more preferably 1:1 to 1:10, and most preferably 1:1 to 1:5.

When the molar ratio of the transition metal complex represented by Formula 6 to the compound represented by Formula 10 or 11 is less than 1:2, the metal compound is insufficiently alkylated since the amount of an alkylating agent is too small. On the other hand, when the molar ratio of the transition metal complex represented by Formula 6 to the compound represented by Formula 10 or 11 is greater than 1:5,000, the metal compound is alkylated, but the remaining excess alkylating agent can react with the activator of Formula 12 so that the alkylated metal compound is less activated. When the molar ratio of the transition metal complex to the compound represented by Formula 12 is less than 1:1, the amount of the activator is relatively small so that the metal compound is less activated. On the other hand, when the molar ratio of the transition metal complex to the compound represented by Formula 12 is greater than 1:25, the metal compound is completely activated but excess activator remains, thus leading to problems that the preparation process for the catalyst composition is expensive, and the purity of the resulting polymer is poor.

In the latter method for preparing the catalyst composition, the molar ratio of the transition metal complex represented by Formula 6 to the compound represented by Formula 12 is preferably 1:10 to 1:10,000, more preferably 1:100 to 1:5,000, and most preferably 1:500 to 1:2,000. When the molar ratio of the transition metal complex represented by Formula 6 to the compound represented by Formula 12 is less than 1:10, the metal compound is insufficiently alkylated since the amount of an alkylating agent is relatively small, thus leading to problems that the activity of the catalyst composition is deteriorated. On the other hand, when the molar ratio of the transition metal complex represented by Formula 6 to the compound represented by Formula 12 is greater than 1:10,000, the metal compound is completely activated but excess activator remains, thus leading to problems that the preparation process for the catalyst composition is expensive, and the purity of the resulting polymer is poor.

A reaction solvent used in the preparation of the activated composition may be a hydrocarbon solvent such as pentane, hexane, and heptane, or an aromatic solvent such as benzene and toluene, but is not limited thereto, and any solvent that is available in the art can be used.

In addition, the transition metal complex represented by Formula 6 and the cocatalyst may be used as loaded on silica or alumina.

The compound represented by Formula 10 is not particularly limited as long as it is an alkylaluminoxane, and it is more preferably methylaluminoxane, ethylaluminoxane, isobutylalminoxane, butylaluminoxane, or the like, and most preferably methylaluminoxane.

The compound represented by Formula 11 is not particularly limited, but preferable examples thereof include trimethylaluminum, triethylaluminum, triisobutylaluminum, tripropylaluminum tributylaluminum, dimethylchloroaluminum triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylalminummethoxide, trimethylboron, triethylboron, triisobutylboron, dripropylboron, and tributylboron. More preferably, the compound is selected from trimethylaluminum triethylaluminum, and triisobutylaluminum.

Examples of the compound represented by Formula 12 may include triethylaummiumtetraphenylboron, tributylaranoniumtetraphenylboron, trimethylammoniumtetraphenylboron, tripropylammoniantetraphenylboron, trimethylammoniumtetra(o,p-dimethylphenyl)boron, tributylammoniantetra(p-trifluoromethylphenypboron, trimethylamouniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniantetraphenylboron, triethylammoniumtetraphenylaluminum, tributylammoniumtetraphenylaluminum, trimethylammoniantetraphenylaluminum, tripropylammoniumtetraphenylaluminum, trimethylammoniumtetra(p-tolyl)aluminum, tripropyl ammoniumtetra(p-tolyl)aluminum, triethylammoniumtetra(o,p-dimethylphenyl)aluminum, tributylammoniumtetra(p-trifluoromethylphenyl)aluminum, trimethylammonumtetra(p-trifluoromethylphenyl)aluminum, tributylanmoniantetrapentafluorophenylaluminum, N,N-diethylaniliniumtetraphenylaluminum, N,N-diethylanliniantetraphenylaluminun, N,N-diethylaniliniumtetrapentafluorophenylaluminum, diethylanailioniumtetrapentatetraphenylaluminum, triphenylphosphoniumtetraphenylaluninum, trimethylphosphoniumtetraphenylaluminum, triethylanuoniumtetraphenylaluminum, tributylaunoniumtetraphenylaluminum, tiimethylammoniumtetraphenylboron, tripropylammomumtetraphenylboron, trimethylammoniumtetra(p-tolypboron, tripropylammoniumtetra(p-tolyl)boron, triethylammoniumtetra(o,p-dimethylphenyl)boron, trimethyllammoniumtetra(o,p-dimethylphenyl)boron, tributylammoniurntetra(p-trifluorcmethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, and triphenylcarboniumtetrapentafluorophenylboron.

It is possible that the catalyst composition comprising the transition metal complex represented by Formula 6, and at least one compound selected from the group consisting of the compounds represented by Formulae 10 to 12 is brought into contact with at least one olefin monomer to prepare a polyolefin homopolymer or copolymer.

A most preferable preparation process using the activated catalyst composition is a solution process, but when the composition is used together with an inorganic support such as silica, it can also be applied in a slurry or gas phase process.

In the preparation process, the activated catalyst composition may be dissolved or diluted in a solvent suitable for olefin polymerization, before being incorporated. Examples of the solvent include a $C_{5-12}$ aliphatic hydrocarbon solvent such as pentane, hexane, heptane, nonane, decane, and isomers thereof; an aromatic hydrocarbon solvent such as toluene and benzene; and a hydrocarbon solvent substituted with a chlorine atom such as dichloromethane and chlorobenzene. The solvent used may be treated with a stroll amount of alkylaluminum to eliminate a small amount of water, air, and the like which poison the catalyst composition, or a cocatalyst can further be used to perform the process.

Examples of the olefin-based monomer which can be polymerized using the metal compounds and the cocatalysts include ethylene, an α-olefin, and a cyclic olefin. A diene olefin-based monomer or a triene olefin-based monomer which have at least two double bonds can also be polymerized. Examples of such the monomers include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidene norbornene, phenylnorbornene, vinyl norbornene, dicyclopentadiene, 1,4-butadiene, 1,5-pentadiene, 1,6-hexadiene, styrene, α-methylstyrene, divinylbenzene, and 3-chloromethyl styrene. At least two kinds of the monomers may be mixed, and copolymerized.

In particular, in the preparation method according to the present invention, the catalyst composition is characterized in that it can be used to copolymerize monomers having large steric hindrance such as ethylene and 1-octene even at a high reaction temperature of 90° C. or higher, thereby obtaining a copolymer having a high molecular weight and a very low density of less than 0.910 g/cc.

In the present specification, the "N-containing, substituted or unsubstituted, aliphatic ring having 5 to 20 carbon atoms or aromatic ring having 5 to 20 carbon atoms" is preferably has a substituent such as a hydrogen atom; a silyl radical; an alkyl radical having 1 to 20 carbon atoms, or an aryl radical having 5 to 20 carbon atoms.

Further, in the present specification, the "silyl radical" is preferably trimethylsilyl or triethylsilyl.

MODE FOR THE INVENTION

Hereinbelow, the present invention will be described in greater detail with reference to the following Examples. Examples are for illustrative purposes only, and are not intended to limit the scope of the present invention.

Synthesis of Ligands and Transition Metal Complexes

Organic reagents and solvents were purchased from Aldrich Co., Inc. and Merck Co., Inc., purified using a standard method, and then used. Each step for synthesis was performed while isolated from air and moisture to improve reproducibility of experiments. In order to demonstrate the structure of compounds, a 400 MHz nuclear magnetic resonance (NMR) and an X-ray spectrometer were used to obtain spectra and diagrams, respectively.

EXAMPLE 1

Preparation of 8-(2,3,4,5-tetramethyl-1,3-cyclopentadienyl)-1,2,3,4-tetrahydroquinoline (Compound 3a)

1,2,3,4-tetrahydroquinoline (13.08 g, 98.24 mmol) and diethylether (150 mL) were put into a Schlenk flask. The Schlenk flask was immersed in a dry ice/acetone cooling bath at −78° C., and shaken for 30 minutes. Then, n-BuLi (n-butyl lithium, 39.3 mL, 2.5 M, 98.24 rural) was introduced thereto using a syringe under nitrogen atmosphere to form a pale yellow slurry. Thereafter, the flask was shaken for 2 hours, and then the flask was warmed to ambient temperature while removing the resulting butane gas. The flask was again immersing into the cooling bath at −78° C., and then a $CO_2$ gas was introduced thereto. As introducing carbon dioxide gas, the slurry gradually disappeared to form a clear solution. The flask was connected into a bubbler to remove the carbon dioxide gas, while raising the temperature to ambient temperature. Thereafter, excess $CO_2$ gas and the solvent were removed under vacuum. The flask was transferred into a dry box, and then pentane was added thereto. The mixture was thoroughly stirred, and then filtered to obtain lithium carbamate (Compound 2a) as white solid compound, where diethylether was coordinated. Here, the yield was 100%.

$^1$H NMR (C6D6, C5D5N): δ 1.90 (t, J=7.2 Hz, 6H, ether), 1.50 (br s, 2H, quin-$CH_2$), 2.34 (br s, 2H, quin-$CH_2$), 3.25 (q, J=7.2 Hz, 4H, ether), 3.87 (br, s, 2H, quin-$CH_2$), 6.76 (br d, J=5.6 Hz, 1H, quin-CH) ppm, $^{13}$C NMR (C6D6): δ 24.24, 28.54, 45.37, 65.95, 121.17, 125.34, 125.57, 142.04, 163.09 (C=O) ppm.

The resulting lithium carbamate compound (Compound 2a) (8.47 g, 42.60 mmol) was put into a Schlenk flask. Thereafter, tetrahydrofuran (4.6 g, 63.9 mmol) and diethylether (45 mL) were added thereto in this order. The Schlenk flask was immersed in an acetone/small amount of dry ice cooling bath at −20° C., and shaken for 30 minutes, and then tert-BuLi (25.1 mL, 1.7 M, 42.60 mmol) was added thereto. At that time, the reaction mixture turned red. While maintaining the temperature at −20° C., the reaction mixture was stirred for 6 hours. A $CeCl_3$.2LiCl solution of tetrahydrofuran (129 mL, 0.33 M, 42.60 mmol) and tetramethylcyclopentanone (5.89 g, 42.60 mmol) were mixed in a syringe, and then introduced into the flask under nitrogen atmosphere. The flask was gradually warmed to ambient temperature, and one hour later, the incubator was removed, and the temperature was maintained at ambient temperature. Then, water (15 mL) was added into the flask, and ethyl acetate was added thereto to obtain a filtrate. The filtrate was transferred into a separatory funnel, and hydrochloric acid (2 N, 80 mL) was added thereto, and the separatory funnel was shaken for 12 minutes. Thereafter, a saturated, aqueous sodium carbonate solution (160 mL) was added thereto to neutralize the solution, and then an organic phase was extracted. To this organic phase, anhydrous magnesium sulfate was added to remove moisture, the resultant was filtered and taken, and the solvent was removed. The resulting filtrate was purified by column chromatography using a hexane/ethyl acetate (v/v, 10:1) solvent to obtain a yellow oil. The yield was 40%.

$^1$H NMR (C6D6): δ 1.00 (br d, 3H, Cp-$CH_3$), 1.63-1.73 (m, 2H, quin-$CH_2$) 1.80 (s, 3H, Cp-$CH_3$), 1.81 (s, 3H, Cp-$CH_3$), 1.85 (s, 3H, Cp-$CH_3$), 2.64 (t, J=6.0 Hz, 2H, quin-$CH_2$), 2.84-2.90 (br, 2H, quin-$CH_2$), 3.06 (br s, 1H, Cp-H), 3.76 (br s, 1H, N—H), 6.77 (t, J=7.2 Hz, 1H, quin-CH), 6.92 (d, J=2.4 Hz, 1H, quin-CH), 6.94 (d, J=2.4 Hz, 1H, quin-CH) ppm.

EXAMPLE 2

Preparation of [(1,2,3,4-tetrahydroquinolin-8-yl) tetramethylcyclopenta-dienyl-eta5,kapa-N]titanium dimethyl (Compound 5a)

In a dry box, the compound 3a (8.07 g, 32.0 mmol) as prepared in Example 1 and diethylether (140 mL) were put into a round flask, and cooled to −30° C. n-BuLi (17.7 g, 2.5 M, 64.0 mmol) was slowly added thereto under stirring. While raising the temperature to ambient temperature, reaction was performed for 6 hours. Thereafter, the mixture was washed with diethylether several times, and filtered to obtain a solid. The remaining solvent was removed under vacuum to obtain a dilithium compound (Compound 4a) (9.83 g) as a yellow solid. The yield was 95%.

$^1$H NMR (C6D6, C5D5N): δ 2.38 (br s, 2H, quin-$CH_2$), 2.53 (br s, 12H, Cp-$CH_3$), 3.48 (br s, 2H, quin-$CH_2$), 4.19 (br s, 2H, quin-$CH_2$), 6.77 (t, J=6.8 Hz, 2H, quin-CH), 7.28 (br s, 1H, quin-CH), 7.75 (br s, 1H, quin-CH) ppm.

In a dry box, $TiCl_4$.DME (4.41 g, 15.76 mmol) and diethylether (150 mL) were put into a round flask, and while stirring the mixture at −30° C., MeLi (21.7 mL, 31.52 mmol, 1.4 M) was slowly added thereto. After stirring the mixture for 15 minutes, the resulting [(1,2,3,4-tetrahydroquinolin-8-yl)tetramethylcyclopenta-dienyl-eta5,kapa-N]dilithium compound (Compound 4a) (5.30 g, 15.76 mmol) was put into the flask. While raising the temperature to ambient temperature, the mixture was stirred for 3 hours. After completion of the reaction, the solvent was removed under vacuum, dissolved in pentane, and then filtered to obtain a filtrate. The pentane was removed under vacuum to obtain a dart brown compound (3.70 g). The yield was 71.3%.

$^1$H NMR (C6D6): δ 0.59 (s, 6H, Ti—$CH_3$), 1.66 (s, 6H, Cp-$CH_3$), 1.69 (br t, J=6.4 Hz, 2H, quin-$CH_2$), 2.05 (s, 6H, Cp-$CH_3$), 2.47 (t, J=6.0 Hz, 2H, quin-$CH_2$), 4.53 (m, 2H, quin-$CH_2$), 6.84 (t, J=7.2 Hz, 1H, quin-CH), 6.93 (d, J=7.6 Hz, quin-CH), 7.01 (d, J=6.8 Hz, quin-CH) ppm. $^{13}$C NMR (C6D6): δ 12.12, 23.08, 27.30, 48.84, 51.01, 119.70, 119.96, 120.95, 126.99, 128.73, 131.67, 136.21 ppm.

EXAMPLE 3

Preparation of 5-indenyl-1,2,3,4-tetrahydroquinoline (Compound 3b)

The procedure was carried out in the same manner as the preparation method of [Example 1] except that indenone was used instead of tetramethylcyclopentanone, and the resultant was purified by column chromatography using a hexane:ethyl acetate (v/v, 20:1) solvent to obtain a yellow oil. The yield was 49%.

$^1$H NMR (C6D6): δ 1.58-1.64 (m, 2H, quin-CH$_2$), 2.63 (t, J=6.8 Hz, 2H, quin-CH$_2$), 2.72-2.77 (m, 2H, quin-CH$_2$), 3.17 (d, J=2.4 Hz, 2H, indenyl-CH$_2$), 3.85 (br s, 1H, N—H), 6.35 (t, J=2.0 Hz, 1H, indenyl-CH), 6.76 (t, J=7.6 Hz, 1H, quin-CH), 6.98 (d, J=7.2 Hz, 1H, quin-CH), 7.17 (td, J=1.6, 7.2 Hz, 1H, quin-CH), 7.20 (td, J=1.6, 7.2 Hz, 2H, indenyl-CH), 7.34 (d, J=7.2 Hz, 1H, indenyl-CH), 7.45 (dd, J=1.2, 6.8 Hz, 1H, indenyl-CH) ppm. $^{13}$C NMR (C6D6): δ 12.12, 23.08, 27.30, 48.84, 51.01, 119.70, 119.96, 120.95, 126.99, 128.73, 131.67, 136.21 ppm.

EXAMPLE 4

Preparation of [(1,2,3,4-tetrahydroquinolin-8-yl)indenyl-eta5,kapa-N]titanium dimethyl (Compound 5b)

A dilithium compound (Compound 4b) was prepared in the same manner as the preparation method of [Example 2] except that 5-indenyl-1,2,3,4-tetrahydroquinoline was used instead of 8-(2,3,4,5-tetramethyl-1,3-cyclopentadienyl)-1,2,3,4-tetrahydroquinoline. The yield was 95%.

$^1$H NMR (C6D6): δ 2.02 (t, J=4.8 Hz, 2H, quin-CH$_2$), 3.15 (t, J=5.6 Hz, 2H, quin-CH$_2$), 3.94 (br s, 2H, quin-CH$_2$), 6.31 (t, J=7.2 Hz, 1H, indenyl-CH), 6.76-6.83 (m, 2H, quin-CH), 6.99 (t, J=7.2, 2.0 Hz, 2H, quin-CH), 7.48 (d, J=7.2 Hz, 2H, indenyl-CH), 8.02 (t, J=8.0 Hz, 2H, indenyl-CH) ppm.

A titanium compound (Compound 5b) was prepared in the same manner as in [Example 2] using the resulting lithium salt compound (Compound 4b). The yield was 47%.

$^1$H NMR (C6D6): δ −0.01 (s, 3H, Ti—CH$_3$), 0.85 (s, 3H, Ti—CH$_3$), 1.56-1.68 (m, 2H, quin-CH$_2$), 2.43 (t, J=6.4 Hz, 2H, quin-CH$_2$), 6.30 (d, J=3.6 Hz, 1H, indenyl-CH), 6.61 (d, J=3.6 Hz, 1H, indenyl-CH), 6.70 (ddd, J=0.8, 68, 8.4 Hz, 1H, indenyl-CH), 6.85 (t, J=7.6 Hz, 1H, quin-CH), 6.95 (tt, J=0.8, 6.8 Hz, 1H, quin-CH), 7.01 (tdd, J=0.8, 68, 8.4 Hz, 2H, indenyl-CH), 7.13-7.17 (m, 1H, quin-CH), 7.48 (d, J=−8.4 Hz, 1H, indenyl-CH) ppm. $^{13}$C NMR (C6D6): δ 22.83, 27.16, 49.35, 55.12, 58.75, 103.36, 119.63, 120.30, 123.18, 125.26, 125.60, 127.18, 127.36, 127.83, 129.13, 129.56, 135.10, 161.74 ppm.

EXAMPLE 5

Preparation of 5-fluorenyl-1,2,3,4-tetrahydroquinoline (Compound 3c)

The procedure was carried out in the same manner as the preparation method of [Example 1] except that fluorenone was used instead of tetramethylcyclopentanone, and the resultant was purified by column chromatography using a hexane:ethyl acetate (v/v 20:1) solvent, and then recrystallized from diethylether to obtain a yellow solid compound. The yield was 56%.

$^1$H NMR (C6D6): δ 1.20 (t, J=7.6 Hz, 2H, quin-CH$_2$), 1.71 (s, 1H, xx), 2.29 (s, 2H, quin-CH$_2$), 2.38 (t, J=6.0 Hz, 2H, quin-CH$_2$), 2.64 (s, 1H, quin-CH$_2$), 2.72 (s, 2H, quin-CH$_2$), 2.30 (s, 1H, N—H), 3.82 (s, 0.5H, N—H), 4.81 (s, 1H, quin-CH), 6.42 (d, J=7.2 Hz, 2H, quin-CH), 6.81 (t, J=7.2 Hz, 1H, quin-CH), 6.94 (dd, J=1.2, 7.2 Hz, 1H, quin-CH), 7.10 (d, J=7.6 Hz, 2H, fluorenyl-CH), 7.23 (t, J=7.2 Hz, 2H, fluorenyl-CH), 7.32 (d, J=7.6 Hz, 2H, fluorenyl-CH), 7.42 (d, J=6.8 Hz, 1H, quin-CH), 7.67 (d, J=7.2 Hz, 2H, fluorenyl-CH) ppm.

EXAMPLE 6

Preparation of [(1,2,3,4-Tetrahydroquinolin-8-yl)fluorenyl-eta5,kapa-N]titanium dimethyl (Compound 5c)

A dilithium compound (Compound 4c) was prepared in the same manner as the preparation method of [Example 2] except that 5-fluorenyl-1,2,3,4-tetrahydroquinoline was used instead of 8-(2,3,4,5-tetramethyl-1,3-cyclopentadienyl)-1,2,3,4-tetrahydroquinoline. The yield was 94%.

$^1$H NMR (C6D6): δ 2.17 (s, 2H, quin-CH$_2$), 3.29-2.26 (m, 2H, quin-CH$_2$), 4.11 (br s, 2H, quin-CH$_2$), 6.31 (t, J=7.2 Hz, 1H, quin-CH), 6.91 (t, J=7.6 Hz, 2H, fluorenyl-CH), 6.99 (d, J=7.2 Hz, 1H, quin-CH), 7.12 (t, J=6.8 Hz, 2H, fluorenyl-CH), 7.58 (dd, J=1.2, 7.6 Hz, 1H, quin-CH), 8.15 (d, J=8.0 Hz, 2H, fluorenyl-CH), 8.57 (d, J=8.0 Hz, 2H, fluorenyl-CH) ppm.

A titanium compound was prepared in the same manner as in [Example 2] using the resulting lithium salt compound (Compound 4c). The yield was 47%.

$^1$H NMR (C6D6): δ 0.14 (s, 6H, Ti—CH$_3$), 1.56-1.68 (m, 2H, quin-CH$_2$), 2.48 (t, J=6.4 Hz, 2H, quin-CH$_2$), 4.18-4.30 (m, 2H, quin-CH$_2$), 6.88-6.96 (m, 3H, CH), 7.04 (d, J=7.6 Hz, 1H, quin-CH), 7.10 (ddd, J=1.2, 68, 8.4 Hz, 2H, fluorenyl-CH), 7.17 (dd, J=0.8, 8.4 Hz, 2H, fluorenyl-CH), 7.28 (d, J=7.2 Hz, 1H, quin-CH), 7.94 (dd, J=0.8, 8.4 Hz, 2H, fluorenyl-CH) ppm. $^{13}$C NMR (C6D6): δ 14.54, 22.76, 27.26, 48.58, 59.65, 111.21, 118.69, 118.98 120.17, 123.34, 123.67, 12616, 12642, 127.75, 129.29, 129.41, 137.28, 160.63 ppm.

EXAMPLE 7

Preparation of 7-(2,3,4,5-Tetramethyl-1,3-cyclopentadienyl)indoline (Compound 3d)

The procedure was carried out in the same manner as the preparation method of [Example 1] except that indoline was used instead of 1,2,3,4-tetrahydroquinoline, and the resultant was purified by column chromatography using a hexane:ethyl acetate (v/v, 20:1) solvent to obtain a yellow oil. The yield was 15%.

$^1$H NMR (C6D6): δ 0.99 (d, J=7.6 Hz, 1H, Cp-CH), 1.82 (s, 3H, Cp-CH$_3$), 1.87 (s, 6H, Cp-CH$_3$), 2.68-2.88 (m, 2H, ind-CH$_2$), 2.91-2.99 (m, 1H, Cp-CH), 3.07-3.16 (m, 3H, ind-CH$_2$N—H), 6.83 (t, J=7.4 Hz, 1H, ind-CH), 6.97 (d, J=7.6 Hz, 1H, ind-CH), 7.19 (d, J=6.8 Hz, 1H, ind-CH) ppm.

EXAMPLE 8

Preparation of [(Indolin-7-yl)tetramethylcyclopentadienyl-eta5,kapa-N]titanium dimethyl (Compound 5d)

A titanium compound was prepared in the same manner as the preparation method of [Example 2] except that 7-(2,3,4,5-tetramethyl-1,3-cyclopentadienyl)indoline was used instead of 8-(2,3,4,5-tetramethyl-1,3-cyclopentadienyl)-1,2,3,4-tetrahydroquinoline. The yield was 71%.

$^1$H NMR (C6D6): δ 0.69 (s, 6H, Ti—CH$_3$), 1.71 (s, 6H, Cp-CH$_3$), 2.04 (s, 6H, Cp-CH$_3$), 2.73 (t, J=8.0 Hz, 2H, ind-CH$_2$), 4.67 (t, J=8.0 Hz, 2H, ind-CH$_2$), 6.82 (t, J=7.2 Hz, 1H, ind-CH), 7.00 (t, J=7.2 Hz, 2H, ind-CH) ppm. $^{13}$C NMR (C6D6): δ 12.06, 12.15, 32.24, 54.98, 56.37, 120.57, 120.64, 121.54, 124.02, 126.52, 126.81, 136.75 ppm.

EXAMPLE 9

Preparation of 2-methyl-8-(2,3,4,5-tetramethyl-1,3-cyclopentadienyl)-1,2,3,4-tetrahydroquinoline (Compound 3e)

The procedure was carried out in the same manner as the preparation method of [Example 1] except that 2-methyl-1,2,3,4-tetrahydroquinoline (5.02 g, 34.1 mmol) was used instead of 1,2,3,4-tetrahydroquinoline. The yield was 51%.

$^1$H NMR (CDCl$_3$): δ 6.89 (d, J=7.2 Hz, 1H, CH), δ 6.74 (d, J=7.2 Hz, 1H, CH), δ 6.57 (t, J=7.4 Hz, 1H, CH), δ 3.76 (br s, 1H, NH), δ 3.45 (br s, 1H, Cp-CH), δ 3.32 (m 1H, quinoline-CH), δ 3.09-2.70 (m, 2H, quinoline-CH$_2$), δ 1.91 (s, 3H, Cp-CH$_3$), δ 1.87 (s, 3H, Cp-CH$_3$), δ 1.77 (s, 3H, Cp-CH$_3$), δ 1.67-1.50 (m, 2H, quinoline-CH$_2$), δ 1.17 (d, J=6.4 Hz, 3H, quinoline-CH$_3$), δ 0.93 (d, J=7.6 Hz, 3H, Cp-CH$_3$) ppm.

EXAMPLE 10

Preparation of [(2-Methyl-1,2,3,4-tetrahydroquinolin-8-yl)tetramethylcyclopenta-dienyl-eta5,kapa-N] titanium (IV) dimethyl (Compound 5e)

A dilithium salt compound (Compound 4e) (4.92 g, 77%) as a pale yellow solid, where 1.17 equivalents of diethyl ether were coordinated, was prepared in the same manner as in [Example 2] except that 2-methyl-8-(2,3,4,5-tetramethyl-1,3-cyclopentadienyl)-1,2,3,4-tetrahydroquinoline (4.66 g, 17.4 mmol) was used instead of 8-(2,3,4,5-tetramethyl-1,3-cyclopentadienyl)-1,2,3,4-tetrahydroquinoline.

$^1$H NMR (Pyridine-d8): δ 7.37 (br s, 1H, CH), δ 7.05 (d, J=6 Hz, 1H, CH), δ 6.40 (t, J=6.8 Hz, 1H, CH), δ 3.93 (br s, 1H, CH), δ 3.27 (m, 1H, CH), δ 3.06 (m, 1H, CH), δ 2.28-2.07 (m, 12H, Cp-CH$_3$), δ 1.99 (m, 1H, CH), δ 1.78 (m, 1H, CH), δ 1.18 (d, J=5.6 Hz, quinoline-CH$_3$) ppm.

A titanium compound (0.56 g, 60%) was prepared in the same manner as in [Example 2] using the resulting dilithium salt compound (Compound 4e) (1.00 g, 2.73 mmol).

$^1$H NMR (CDCl$_3$): δ 6.95 (d, J=8 Hz, 1H, CH), δ 6.91 (d, J=8 Hz, 1H, CH), δ 6.73 (t, J=8 Hz, 1H, CH), δ 5.57 (m, 1H, CH), δ 2.83 (m, 1H, CH), δ 2.55 (m, 1H, CH), δ 2.24 (s, 3H, Cp-CH$_3$), δ 2.20 (s, 3H, Cp-CH$_3$), δ 1.94-1.89 (m, 1H, CH), δ 1.83-1.75 (m, 1H, CH), δ 1.70 (s, 3H, Cp-CH$_3$), δ 1.60 (s, 3H, Cp-CH$_3$), δ 1.22 (d, J=6.8 Hz, 3H, quinoline-CH$_3$), δ 0.26 (d, J=6.8 Hz, 6H, TiMe$_2$-CH$_3$) ppm.

EXAMPLE 11

Preparation of 6-methyl-8-(2,3,4,5-tetramethyl-1,3-cyclopentadienyl)-1,2,3,4-tetrahydroquinoline (Compound 3f)

The procedure was carried out in the same manner as the preparation method of [Example 1] except that 6-methyl-1,2,3,4-tetrahydroquinoline (5.21 g, 35.4 mmol) was used instead of 1,2,3,4-tetrahydroquinoline. The yield was 34%.

$^1$H NMR (CDCl$_3$): δ 670 (s, 1H, CH), δ 6.54 (s, 1H, CH), δ 3.71 (br s, 1H, NH), δ 3.25-3.05 (m, 3H, Cp-CH, quinoline-CH$_2$), δ 2.76 (t, J=6.4 Hz, 2H, quinoline-CH$_2$), δ 2.19 (s, 3H, CH$_3$), δ 1.93-1.86 (m, 2H, quinoline-CH$_2$), δ 1.88 (s, 3H, Cp-CH$_3$), δ 1.84 (s, 3H, Cp-CH$_3$), δ 1.74 (s, 3H, Cp-CH$_3$), δ 0.94 (br d, J=6.8 Hz, 3H, Cp-CH$_3$) ppm.

EXAMPLE 12

Preparation of [(6-methyl-1,2,3,4-tetrahydroquinolin-8-yl)tetramethylcyclopenta-dienyl-eta5,kapa-N] titanium dimethyl (Compound 5f)

A dilithium salt compound (Compound 4f) (2.56 g, 58%) as a pale yellow solid, where 1.15 equivalents of diethyl ether were coordinated, was prepared in the same manner as in [Example 2] except that 6-methyl-8-(2,3,4,5-tetramethyl-1,3-cyclopentadienyl)-1,2,3,4-tetrahydroquinoline (3.23 g, 12.1 mmol) was used instead of 8-(2,3,4,5-tetramethyl-1,3-cyclopentadienyl)-1,2,3,4-tetrahydroquinoline.

$^1$H NMR (Pyridine-d8): δ 7.02 (br s, 1H, CH), δ 6.81 (s, 1H, CH), δ 3.94 (m, 2H, CH$_2$), δ 3.19 (m, 2H, CH$_2$), δ 2.52-2.10 (m, 17H, CH$_2$, quinoline-CH$_3$, Cp-CH$_3$) ppm.

A titanium compound (0.817 g, 58%) was prepared in the same manner as in [Example 2] using the resulting dilithium salt compound (Compound 4f) (1.50 g, 4.12 mmol).

$^1$H NMR (C$_6$D$_6$): δ 6.87 (s, 1H, CH), δ 6.72 (s, 1H, CH), δ 4.57 (m, 2H, CH$_2$), δ 2.45 (t, J=6.2 Hz, 2H, CH$_2$), δ 2.24 (s, 3H, quinoline-CH$_3$), δ 2.05 (s, 6H, Cp-CH$_3$), δ 1.72-1.66 (m, 2H, CH$_2$), δ 1.69 (s, 6H, Cp-CH$_3$), δ 0.57 (s, 6H, TiMe$_2$-CH$_3$) ppm.

EXAMPLE 13

Preparation of 2-methyl-7-(2,3,4,5-tetramethyl-1,3-cyclopentadienyl)indoline (Compound 3g)

The procedure was carried out in the same manner as in [Example 1] except that 2-methylindoline (6.23 g, 468 mmol) was used instead of 1,2,3,4-tetrahydroquinoline. The yield was 19%.

$^1$H NMR (CDCl$_3$): δ 6.97 (d, J=7.2 Hz, 1H, CH), δ 6.78 (d, J=8 Hz, 1H, CH), δ 6.67 (t, J=7.4 Hz, 1H, CH), δ 3.94 (m, 1H, quinoline-CH), δ 3.51 (br s, 1H, NH), δ 3.24-3.08 (m, 2H, quinoline-CH$_2$, Cp-CH), δ 2.65 (m, 1H, quinoline-CH$_2$), δ 1.89 (s, 3H, Cp-CH$_3$), δ 1.84 (s, 3H, Cp-CH$_3$), δ 1.82 (s, 3H, Cp-CH$_3$), δ 1.13 (d, J=6 Hz, 3H, quinoline-CH$_3$), δ 0.93 (3H, Cp-CH$_3$) ppm.

EXAMPLE 14

Preparation of [(2-methyl indolin-7-yl)tetramethyl-cyclopentadienyl-eta5,kapa-N]titanium dimethyl (Compound 5g)

A dilithium salt compound (Compound 4g) (1.37 g, 50%), where 0.58 equivalent of diethyl ether was coordinated, was prepared in the same manner as in [Example 2] except that 2-methyl-7-(2,3,4,5-tetramethyl-1,3-cyclopentadienyl)-indoline (2.25 g, 8.88 mmol) was used instead of 8-(2,3,4,5-tetramethyl-1,3-cyclopentadienyl)-1,2,3,4-tetrahydroquinoline.

$^1$H NMR (Pyridine-d8): δ 7.22 (br s, 1H, CH), δ 7.18 (d, J=6 Hz, 1H, CH), δ 6.32 (t, 1H, CH), δ 4.61 (br s, 1H, CH), δ 3.54 (m, 1H, CH), δ 3.00 (m, 1H, CH), δ 2.35-2.12 (m, 13H, CH, Cp-CH$_3$), δ 1.39 (d, indoline-CH$_3$) ppm.

A titanium compound was prepared in the same manner as in [Example 2] using the resulting dilithium salt compound (Compound 4g) (1.37 g, 4.44 mmol).

$^1$H NMR (C$_6$D$_6$): δ 7.01-6.96 (m, 2H, CH), δ 6.82 (t, J=7.4 Hz, 1H, CH), δ 4.96 (m, 1H, CH), δ 2.88 (m, 1H, CH), δ 2.40 (m, 1H, CH), δ 2.02 (s, 3H, Cp-CH$_3$), δ 2.01 (s, 3H, Cp-CH$_3$),

δ 1.70 (s, 3H, Cp-CH₃), δ 1.69 (s, 3H, Cp-CH₃), δ 1.65 (d, J=6.4 Hz, 3H, indoline-CH₃), δ 0.71 (d, J=10 Hz, 6H, TiMe₂-CH₃) ppm.

EXAMPLE 15

Preparation of N,N'-1-(2,3,4,5-tetramethyl-1,3-cyclopentadienyl)phenylethylamine (Compound 3h)

The procedure was carried out in the same manner as in [Example 1] except that 2-methylindoline (6.23 g, 46.8 mmol) was used instead of 1,2,3,4-tetrahydroquinoline. Column chromatography using a hexane:ethyl acetate (v/v 20:1) solvent was performed to obtain a yellow oil. The yield was 45%.

$^1$H NMR (C6D6): δ 0.88 (t, J=6.4 Hz, 3H, Et-CH₃), 0.99 (d, J=7.7 Hz, 3H, Cp-CH₃), 1.77 (s, 3H, Cp-CH₃), 1.79 (s, 3H, Cp-CH₃), 1.83 (s, 3H, Cp-CH₃), 2.79-2.94 (m, 2H, Et-CH₂), 3.05 (br m, 1H, Cp-CH), 3.74 (br m, 1H, N—H), 6.66 (d, J=8.0 Hz, 1H, Ph-H), 6.84 (t, J=7.2 Hz, 1H, Ph-H), 7.07 (dd, J=1.2 7.2 Hz, 1H, Ph-H), 7.25 (t, J=7.2 Hz, 1H, Ph-H) ppm.

EXAMPLE 16

Preparation of [Phenylene(tetramethylcyclopentadienyl)(ethylamido)]titanium dimethyl (Compound 5h)

A dilithium salt compound (Compound 40 as a pale yellow solid, where 0.58 equivalent of diethyl ether was coordinated, was prepared in the same manner as in [Example 2] except that N,N'-1-(2,3,4,5-tetramethyl-1,3-cyclopentadienyl)phenylethylamine was used instead of 8-(2,3,4,5-tetramethyl-1,3-cyclopentadienyl)-1,2,3,4-tetrahydroquinoline. The yield was 82%.

$^1$H NMR (C6D6, C5D5N): δ 1.25 (br s, 3H, Et-CH₃), 2.03 (br s, 6H, Cp-CH₃), 2.18 (br s, 6H, Cp-CH₃), 3.43 (br s, 2H, Et-CH₂), 6.40 (br s, 1H, Ph-H), 6.65 (br s, 1H, Ph-H), 7.27 (br s, 1H, Ph-H), 7.53 (br s, 1H, Ph-H) ppm. $^{13}$C NMR (C6D6, C5D5N): δ 11.63, 12.16, 18.90, 45.15, 104.50, 105.82, 106.41, 131.28, 163.39 ppm.

A titanium compound was prepared in the same manner as in [Example 2] using the resulting dilithium salt compound (Compound 4h). The yield was 66%.

$^1$H NMR (C6D6): δ 0.56 (s, 6H, Ti—CH₃), 1.20 (t, J=7.2 Hz, 3H, Et-CH₃), 1.58 (s, 6H, Cp-CH₃), 2.03 (s, 6H, Cp-CH₃), 4.48 (q, J=7.2 Hz, 2H, Et-CH₂), 6.27 (d, J=8.0 Hz, 1H, Ph-H), 6.88 (t, J=7.2 Hz, 1H, Ph-H), 7.12 (d, J=7.2 Hz, 1H, Ph-H), 7.20 (t, J=7.2 Hz, 1H, Ph-H) ppm. $^{13}$C NMR (C6D6): δ 12.03, 12.09, 14.14, 41.29, 50.89, 108.60, 119.82, 121.12, 128.70, 129.27, 136.08, 163.40 ppm.

EXAMPLE 17

Preparation of N,N'-1-(2,3,4,5-tetramethyl-1,3-cyclopentadienyl)phenyl-iso-propylamine (Compound 3i)

The procedure was carried out in the same manner as in [Example 1] except that 2-methylindoline (6.23 g, 46.8 mmol) was used instead of 1,2,3,4-tetrahydroquinoline. Column chromatography using a hexane:toluene (v/v 2:1) solvent was performed to obtain a yellow oil. The yield was 16%.

$^1$H NMR (C6D6): δ 0.91 (d, J=6.0 Hz, 2H, Cp-CH₃), 0.94-1.05 (m, 6H, iPr-CH₃), 1.76 (s, 3H, Cp-CH₃), 1.80 (s, 3H, Cp-CH₃), 1.82 (s, 3H, Cp-CH₃), 3.02 (br 1H, Cp-CH), 3.37-3.50 (m, 1H, iPr-CH), 3.74 (br s, 1H, N—H), 6.66 (d, J=8.0 Hz, 1H, Ph-CH), 6.81 (t, J=7.2 Hz, 1H, Ph-CH), 7.06 (dd, J=1.6 7.2 Hz, 1H, Ph-CH), 7.23 (t, J=7.2 Hz, 1H, Ph-CH) ppm.

EXAMPLE 18

Preparation of [Phenylene(tetramethylcyclopentadienyl)(iso-propylamido)]titanium dimethyl (Compound 5i)

A dilithium salt compound (Compound 4i) was prepared in the same manner as in [Example 2] except that N,N'-1-(2,3,4,5-tetramethyl-1,3-cyclopentadienyl)phenyl-iso-propylamine) was used instead of 8-(2,3,4,5-tetramethyl-1,3-cyclopentadienyl)-1,2,3,4-tetrahydroquinoline. The yield was 87%.

$^1$H NMR (C6D6, C5D5N): δ 1.21 (br s, 6H, iPr-CH₃), 1.89 (br s, 6H, Cp-CH₃), 2.14 (br s, 6H, Cp-CH₃), 3.84 (br s, 1H, iPr-CH), 6.34 (br s, 1H, Ph-CH), 6.68 (br s, 1H, Ph-CH), 7.21-7.57 (br m, 2H, Ph-CH) ppm. $^{13}$C NMR (C6D6, C5D5N): δ 11.49, 12.11, 26.06, 47.54, 103.81, 106.55, 108.42, 131.60, 162.49 ppm.

A titanium compound was prepared in the same manner as in [Example 2] using the resulting dilithium salt compound (Compound 4i). The yield was 77%.

COMPARATIVE EXAMPLE 1

Preparation of dimethylsilyl-butylamido)(tetramethylcyclopentadienyl)titanium dichloride (Compound 33)

A dimethylsilyl(t-butylamido)(tetramethylcyclopentadienyl)titanium dichloride transition metal complex was purchased from Boulder Scientific, Inc. (U.S.A.), and directly used for the ethylene copolymerization.

Ethylene Copolymerization

EXAMPLE 19

Copolymerization of High-Pressure ethylene and 1-butene

A hexane solvent (1.0 L) and an appropriate amount of 1-butene comonomers were charged into a 2 L autoclave reactor. The reactor was heated to 150° C. that was a polymerization temperature, and was filled with about 35 bar of ethylene. The titanium transition metal complex (1.0 μmol, Al/Ti=25) (Compound 5a) treated with an appropriate amount of a triisobutylaluminum compound and a dimethylaniliniumtetrakis(pentafluorophenyl)borate cocatalyst solution (B/Ti=5) were added to a catalyst injecting cylinder, and then injected into the reactor. Polymerization was performed for 10 minutes by continuously injecting ethylene in order to maintain the pressure in the reactor between 34 bar to 35 bar. Heat generated from the reaction was removed through a cooling coil installed in the reactor, and the temperature was maintained as constant as possible. After the polymerization, the polymer solution was discharged to the lower portion of the reactor, and cooled using excess ethanol. The obtained polymer was dried for over 12 hours or more in a vacuum oven. The experiment results are shown in Table 1.

EXAMPLE 20 to EXAMPLE 28

Copolymerization of High-Pressure Ethylene and 1-butene

Copolymerization was performed in the same manner as in [Example 19] except that the transition metal complexes (Compound 5b, 5c, 5d, 5e, 5f, 5g, 5h, and 5i) as prepared in the above Examples were used instead of the transition metal complex, Compound 5a, as prepared in [Example 2]. However, in Example 28, the polymerization temperature was 120° C. The experiment results are shown in Table 1.

COMPARATIVE EXAMPLE 2 to COMPARATIVE EXAMPLE 3

Copolymerization of High-Pressure Ethylene and 1-butene

Copolymerization was performed in the same manner as in [Example 19] except that the transition metal complex (Compound 33) as obtained in [Comparative Example 1] was used instead of Compound 5a as prepared in [Example 2]. However, in Comparative Example 3, the polymerization temperature was 120° C. The experiment results are shown in Table 1.

Evaluation on Properties (Weight, Activity, Melt Index, Melting Point, and Density)

A melt index (MI) of a polymer was measured in accordance with ASTM D-1238 (Conditions: E, 190° C., 2.16 Kg load). A melting point (Tm) of a polymer was measured using a Differential Scanning calorimeter (DSC) 2920 manufactured by TA Inc. That is, the temperature was increased to 200° C., maintained at 200° C. for 5 minutes, and decreased to 30° C. Then, the temperature was increased again, and the summit of the DSC curve was measured as the melting point. Here, the temperature was increased and decreased by 10° C./min, and the melting point was obtained in a second temperature increase period.

In order to measure the density of a polymer, a sample that had been treated with an antioxidant (1,000 ppm) was formed into a sheet having a thickness of 3 mm and a radius of 2 in by a 180° C. press maid, and then the prepared sheet was cooled by 10° C./min. The cooled sheet was measured using a mettler scale.

The various properties of the copolymers obtained in Examples 19 to 28, and Comparative Examples 2 and 3 were measured, and the results are shown in Table 1.

As shown in Table 1, most of the transition metal complexes of Examples according to the present invention provided copolymers having relatively higher molecular weights and lower densities, as compared with those of Comparative Examples, when 1-butene and ethylene was copolymerized.

Accordingly, it is confirmed that the transition metal complexes according to the present invention have relatively excellent reactivity for olefin monomers having large steric hindrance such as 1-butene.

Particularly, the transition metal complexes (Compounds 5a, 5e, and 5f) used in Example 19, 23, and 24 showed equal or higher catalyst activity, as compared to the transition metal complex (Compound 33) used in Comparative Examples. Further, in the polymerization at 120° C., the transition metal complexes (Compounds 5a, 5e, and 5f) used in Examples 19, 23, and 24 showed higher catalyst activity, and the obtained copolymers had higher molecular weights and lower densities, as compared to the transition metal complex (Compound 33) used in Comparative Examples.

The invention claimed is:

1. A transition metal complex represented by Formula 6 below:

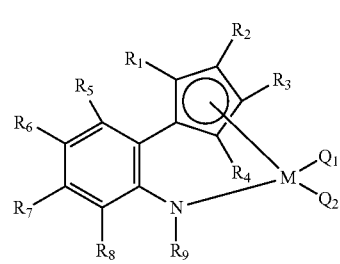

<Formula 6> wherein $R_1$, $R_2$, $R_3$, and $R_4$ are each independently an alkyl radical having 1 to 20 carbon atoms or an alkenyl radical having 2 to 20 carbon atoms; at least two of $R_1$, $R_2$, $R_3$, and $R_4$ are connected to each other to form an aromatic ring having 5 to 20 carbon atoms;

$R_5$, $R_6$, $R_7$, and $R_8$ are each independently a hydrogen atom; a halogen radical; or an alkyl radical having 1 to 20 carbon atoms or an aryl radical having 5 to 20 carbon

TABLE 1

Results of copolymerization of ethylene and 1-butene

| Example | Transition metal complexes used | 1-Butene (M) | Activity (kg/mmol-Ti) | Melt index[a] (g/10 min) | Melt index[b] (g/10 min) | Density (g/cc) |
|---|---|---|---|---|---|---|
| Example 19 | Compound 5a | 1.6 | 43.7 | 3.5 | 28.8 | 0.859 |
| Example 20 | Compound 5b | 1.6 | 3.4 | 0 | 0 | 0.870 |
| Example 21 | Compound 5c | 1.6 | 16.6 | 0 | 0 | 0.860 |
| Example 22 | Compound 5d | 1.6 | 15.3 | 0 | 0.66 | 0.873 |
| Example 23 | Compound 5e | 1.6 | 36.0 | 15.4 | — | 0.862 |
| Example 24 | Compound 5f | 1.6 | 29.8 | 1.3 | 12.5 | 0.860 |
| Example 25 | Compound 5g | 1.6 | 22.1 | 0 | 0.8 | 0.873 |
| Example 26 | Compound 5h | 1.6 | 22.0 | 1.4 | 15.8 | 0.866 |
| Example 27 | Compound 5i | 1.6 | 8.5 | 0 | 0 | 0.876 |
| Comparative Example 2 | Compound 33 | 1.6 | 30.5 | 5.9 | 59 | 0.900 |
| Example 28 | Compound 5a[c] | 1.2 | 57.5 | 0 | 1.3 | 0.881 |
| Comparative Example 3 | Compound 33[c] | 1.2 | 44.1 | 0 | 1.2 | 0.902 |

[a]$I_2$ value,
[b]$I_{21.6}$ value,
[c]Polymerization at 120° C.

atoms; and at least two of $R_5$, $R_6$, $R_7$, and $R_8$ are optionally connected to each other to form an aliphatic ring having 5 to 20 carbon atoms or an aromatic ring having 5 to 20 carbon atoms;

$R_9$ is a hydrogen atom; a branched or linear alkyl radical having 2 to 3 carbon atoms; or an aryl radical having 5 to 20 carbon atoms;

M is a transition metal belonging to Group 4; and $Q_1$ and $Q_2$ are an alkyl radical having 1 to 20 carbon atoms.

2. The transition metal complex according to claim 1, wherein the transition metal complex is represented by one of the structural formulae as shown below:

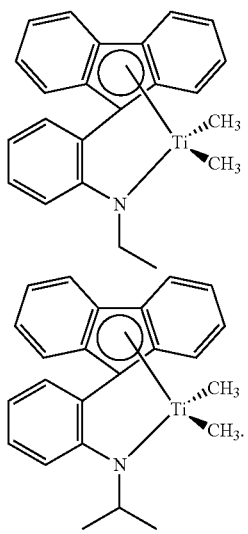

3. A catalyst composition comprising:
the transition metal complex represented by Formula 6 of claim 1; and
at least one cocatalyst compound selected from the group consisting of the compounds represented by Formulae 10, 11, and 12 below:

—[Al($R_{22}$)—O]$_a$—         <Formula 10> wherein $R_{22}$'s are each independently a halogen radical; a hydrocarbyl radical having 1 to 20 carbon atoms; or a hydrocarbyl radical having 1 to 20 carbon atoms substituted with halogen; and a is an integer of no less than 2;

D($R_{22}$)$_3$         <Formula 11> wherein D is aluminum or boron; and $R_{22}$'s are each independently as defined above;

[L—H]$^+$[Z(A)$_4$]$^-$ or [L]$^+$[Z(A)$_4$]$^-$         <Formula 12> wherein L is a neutral or cationic Lewis acid; H is a hydrogen atom; Z is an element belonging to Group 13; A's are each independently an aryl radial having 6 to 20 carbon atoms or alkyl radical having 1 to 20 carbon atoms, substituted with one or more hydrogen atoms; and the substituent is a halogen, a hydrocarbyl radical having 1 to 20 carbon atoms, an alkoxy radical having 1 to 20 carbon atoms, or an aryloxy radical having 6 to 20 carbon atoms.

4. The catalyst composition according to 3, wherein the transition metal complex represented by Formula 6 is represented by Formula 9 below:

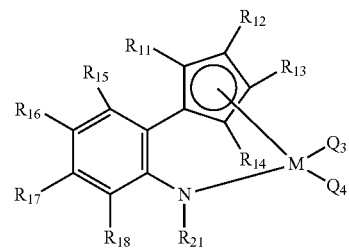

<Formula 9> wherein $R_{11}$, $R_{12}$, $R_{13}$, and $R_{14}$ are each independently an alkyl radical having 1 to 20 carbon atoms or an alkenyl radical having 2 to 20 carbon atoms; and at least two of $R_{11}$, $R_{12}$, $R_{13}$, and $R_{14}$ are connected to each other to form an aromatic ring having 5 to 20 carbon atoms;

$R_{15}$, $R_{16}$, $R_{17}$, and $R_{18}$ are each independently a hydrogen atom; a halogen radical; an alkyl radical having 1 to 20 carbon atoms or an aryl radical having 5 to 20 carbon atoms; and at least two of $R_{15}$, $R_{16}$, $R_{17}$, and $R_{18}$ are optionally connected to each other to form an aliphatic ring having 5 to 20 carbon atoms or an aromatic ring having 5 to 20 carbon atoms;

$R_{21}$ is a hydrogen atom; a branched, linear, or cyclic alkyl radical having 1 to 20 carbon atoms; or an aryl radical having 5 to 20 carbon atoms;

M is a transition metal belonging to Group 4; and $Q_3$ and $Q_4$ are an alkyl radical having 1 to 20 carbon atoms.

5. The catalyst composition according to claim 3, wherein the transition metal complex represented by Formula 6 is represented by one of the structural formulae as shown below:

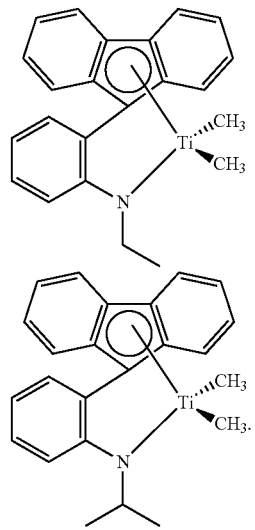

6. The catalyst composition according to claim 3, wherein the molar ratio of the transition metal complex represented by Formula 6 to the compound represented by Formula 10 or 11 is 1:2 to 1:5000, and the molar ratio of the transition metal complex represented by Formula 6 to the compound represented by Formula 12 is 1:1 to 1:25.

* * * * *